United States Patent
Bickley et al.

(10) Patent No.: US 9,474,618 B2
(45) Date of Patent: Oct. 25, 2016

(54) METHOD AND APPARATUS FOR RESTORING A JOINT, INCLUDING THE PROVISION AND USE OF A LONGITUDINALLY-ADJUSTABLE AND ROTATIONALLY-ADJUSTABLE JOINT PROSTHESIS

(71) Applicant: Simplicity Orthopedics, Inc., North Andover, MA (US)

(72) Inventors: Barry T. Bickley, North Andover, MA (US); Richard E. Zovich, Kensington, CT (US); Aldo M. Zovich, East Hampton, CT (US)

(73) Assignee: Simplicity Orthopedics, Inc., North Andover, MA (US)

( * ) Notice: Subject to any disclaimer, the term of this patent is extended or adjusted under 35 U.S.C. 154(b) by 0 days.

(21) Appl. No.: 14/148,880

(22) Filed: Jan. 7, 2014

(65) Prior Publication Data

US 2014/0324185 A1    Oct. 30, 2014

Related U.S. Application Data

(63) Continuation of application No. 12/903,079, filed on Oct. 12, 2010, now Pat. No. 8,623,092.

(60) Provisional application No. 61/278,782, filed on Oct. 10, 2009, provisional application No. 61/368,424, filed on Jul. 28, 2010.

(51) Int. Cl.
*A61F 2/30* (2006.01)
*A61F 2/40* (2006.01)

(52) U.S. Cl.
CPC ............ *A61F 2/40* (2013.01); *A61F 2002/305* (2013.01); *A61F 2002/3054* (2013.01);

(Continued)

(58) Field of Classification Search
CPC ............... A61F 2/40; A61F 2002/40; A61F 2002/305; A61F 2002/30495; A61F 2002/30507; A61F 2002/30515; A61F 2002/30401; A61F 2002/30403; A61F 2002/30405; A61F 2002/4044; A61F 2002/4066
USPC .......... 623/17.11–19.14, 23.45–23.47, 11.11, 623/16.11, 20.14, 20.15, 20.32, 20.36, 623/21.12, 21.18, 22.11, 22.4, 22.43, 23.11, 623/22.46, 23.15, 23.23, 23.39, 23.44, 27, 623/33, 38; 606/62, 63, 66, 258
See application file for complete search history.

(56) References Cited

U.S. PATENT DOCUMENTS 1,934,910 A * 11/1933 Buhr ......................... 279/105.1
3,906,552 A *  9/1975 Weber ............................ 623/47

(Continued)

FOREIGN PATENT DOCUMENTS

WO    WO 2008/048195    4/2008

*Primary Examiner* — Alvin Stewart
(74) *Attorney, Agent, or Firm* — Pandiscio & Pandiscio

(57) ABSTRACT

A joint prosthesis for mounting in a first bone and presenting a prosthetic joint surface for engaging an opposing joint surface of a second bone, the joint prosthesis comprising a sleeve which is adapted for partial disposition in an opening formed in the first bone; a center adapter which is adapted for disposition within the sleeve and a prosthetic joint surface mounted to the center' adapter; wherein the disposition of the center adapter is adjustable, both longitudinally and rotationally, relative to the sleeve, so that the disposition of the 15 prosthetic joint surface is adjustable, both longitudinally and rotationally, relative to the opposing joint surface of the second bone.

16 Claims, 36 Drawing Sheets

(52) U.S. Cl.
CPC ............. *A61F 2002/3055* (2013.01); *A61F 2002/30495* (2013.01); *A61F 2002/30507* (2013.01); *A61F 2002/30515* (2013.01); *A61F 2002/30551* (2013.01); *A61F 2002/30909* (2013.01); *A61F 2002/4044* (2013.01); *A61F 2002/4066* (2013.01); *A61F 2220/0025* (2013.01)

(56) References Cited

U.S. PATENT DOCUMENTS

| | | | |
|---|---|---|---|
| 3,947,897 A * | 4/1976 | Owens | 623/11.11 |
| 3,976,060 A * | 8/1976 | Hildebrandt et al. | 606/241 |
| 4,262,665 A * | 4/1981 | Roalstad et al. | 606/62 |
| 4,275,717 A * | 6/1981 | Bolesky | 606/63 |
| 4,453,539 A * | 6/1984 | Raftopoulos et al. | 606/63 |
| 4,502,160 A * | 3/1985 | Moore et al. | 623/23.45 |
| 4,536,898 A * | 8/1985 | Palfray | 623/33 |
| 4,892,546 A * | 1/1990 | Kotz et al. | 623/23.45 |
| 4,908,032 A * | 3/1990 | Keller | 623/23.45 |
| 4,931,055 A * | 6/1990 | Bumpus et al. | 606/60 |
| 4,938,768 A * | 7/1990 | Wu | 623/23.47 |
| 5,004,476 A * | 4/1991 | Cook | 623/23.3 |
| 5,041,116 A * | 8/1991 | Wilson | 606/65 |
| 5,263,955 A * | 11/1993 | Baumgart et al. | 606/63 |
| 5,330,531 A * | 7/1994 | Capanna | 623/19.14 |
| 5,334,202 A * | 8/1994 | Carter | 606/58 |
| 5,358,524 A * | 10/1994 | Richelsoph | 623/23.47 |
| 5,364,396 A * | 11/1994 | Robinson et al. | 606/53 |
| 5,376,129 A * | 12/1994 | Faulkner et al. | 623/33 |
| 5,387,239 A * | 2/1995 | Bianco et al. | 623/23.45 |
| 5,415,660 A * | 5/1995 | Campbell et al. | 606/62 |
| 5,429,638 A * | 7/1995 | Muschler et al. | 606/60 |
| 5,466,261 A * | 11/1995 | Richelsoph | 623/23.47 |
| 5,505,733 A * | 4/1996 | Justin et al. | 606/63 |
| 5,507,837 A * | 4/1996 | Laghi | 623/38 |
| 5,516,335 A * | 5/1996 | Kummer et al. | 606/63 |
| 5,545,230 A * | 8/1996 | Kinsinger et al. | 623/38 |
| 5,575,790 A * | 11/1996 | Chen et al. | 606/60 |
| 5,626,579 A * | 5/1997 | Muschler et al. | 606/60 |
| 5,645,607 A * | 7/1997 | Hickey | 623/23.35 |
| 5,653,764 A * | 8/1997 | Murphy | 623/23.15 |
| 5,702,457 A | 12/1997 | Walch et al. | |
| 5,702,479 A * | 12/1997 | Schawalder | 623/23.15 |
| 5,704,939 A * | 1/1998 | Justin | 606/63 |
| 5,728,170 A * | 3/1998 | Becker et al. | 623/37 |
| 5,800,564 A * | 9/1998 | Gelineau | 623/38 |
| 5,888,232 A * | 3/1999 | Taylor | 623/38 |
| 5,904,722 A * | 5/1999 | Caspers | 623/34 |
| 5,906,644 A * | 5/1999 | Powell | 623/20.15 |
| 5,928,230 A * | 7/1999 | Tosic | 606/57 |
| 5,928,290 A * | 7/1999 | Gramnas | 623/33 |
| 5,931,872 A * | 8/1999 | Lohmann | 623/36 |
| 5,951,554 A * | 9/1999 | Holmes | 606/104 |
| 5,961,555 A * | 10/1999 | Huebner | 623/19.11 |
| 5,971,729 A * | 10/1999 | Kristinsson et al. | 425/2 |
| 5,980,576 A * | 11/1999 | Graf et al. | 623/33 |
| 6,033,412 A * | 3/2000 | Losken et al. | 606/105 |
| 6,033,439 A * | 3/2000 | Camino et al. | 623/19.11 |
| 6,045,582 A * | 4/2000 | Prybyla | 623/19.11 |
| 6,051,026 A * | 4/2000 | Biedermann et al. | 623/38 |
| 6,063,125 A * | 5/2000 | Arbogast et al. | 623/34 |
| 6,106,559 A * | 8/2000 | Meyer | 623/33 |
| 6,123,732 A * | 9/2000 | Gramnas | 623/38 |
| 6,176,881 B1 | 1/2001 | Schar et al. | 623/17.11 |
| 6,200,317 B1 * | 3/2001 | Aalsma et al. | 606/62 |
| 6,228,120 B1 * | 5/2001 | Leonard et al. | 623/19.12 |
| 6,235,062 B1 * | 5/2001 | Gramnas | 623/33 |
| 6,267,787 B1 * | 7/2001 | Capper et al. | 623/36 |
| 6,287,345 B1 * | 9/2001 | Slemker et al. | 623/34 |
| 6,319,286 B1 * | 11/2001 | Fernandez et al. | 623/23.18 |
| 6,334,876 B1 * | 1/2002 | Perkins | 623/34 |
| 6,336,929 B1 * | 1/2002 | Justin | 606/63 |
| 6,361,569 B1 * | 3/2002 | Slemker et al. | 623/33 |
| 6,398,817 B1 * | 6/2002 | Hellberg et al. | 623/38 |
| 6,402,789 B1 * | 6/2002 | Gramnas | 623/38 |
| 6,416,516 B1 * | 7/2002 | Stauch et al. | 606/62 |
| 6,440,171 B1 * | 8/2002 | Doubler et al. | 623/22.42 |
| 6,440,173 B1 * | 8/2002 | Meyer | 623/36 |
| 6,485,522 B1 * | 11/2002 | Grundei | 623/38 |
| 6,508,841 B2 * | 1/2003 | Martin et al. | 623/23.12 |
| 6,524,342 B1 * | 2/2003 | Muhlhausler et al. | 623/19.14 |
| 6,565,576 B1 * | 5/2003 | Stauch et al. | 606/105 |
| 6,569,203 B1 * | 5/2003 | Keller | 623/23.47 |
| 6,576,021 B2 * | 6/2003 | Laghi | 623/33 |
| 6,579,323 B2 | 6/2003 | Laghi | |
| 6,589,288 B2 * | 7/2003 | McDowell et al. | 623/33 |
| 6,589,289 B2 * | 7/2003 | Ingimarsson | 623/33 |
| 6,596,027 B2 | 7/2003 | Laghi | |
| 6,596,028 B1 | 7/2003 | Laghi | |
| 6,673,079 B1 * | 1/2004 | Kane | 606/105 |
| 6,673,114 B2 * | 1/2004 | Hartdegen et al. | 623/19.12 |
| 6,679,921 B2 * | 1/2004 | Grubbs | 623/33 |
| 6,689,171 B2 * | 2/2004 | Slemker et al. | 623/33 |
| 6,706,042 B2 * | 3/2004 | Taylor | 606/57 |
| 6,716,250 B2 * | 4/2004 | Ganjianpour | 623/22.42 |
| 6,761,743 B1 * | 7/2004 | Johnson | 623/38 |
| 6,796,984 B2 * | 9/2004 | Soubeiran | 606/300 |
| 6,849,076 B2 * | 2/2005 | Blunn et al. | 606/105 |
| 6,893,463 B2 * | 5/2005 | Fell et al. | 623/14.12 |
| 6,893,468 B2 * | 5/2005 | Lund | 623/36 |
| 6,953,478 B2 * | 10/2005 | Bouttens et al. | 623/19.11 |
| 6,966,933 B2 * | 11/2005 | Christensen | 623/47 |
| 6,972,042 B2 * | 12/2005 | Benson | 623/38 |
| 7,070,622 B1 * | 7/2006 | Brown et al. | 623/20.14 |
| 7,083,654 B2 * | 8/2006 | Helenberger et al. | 623/33 |
| 7,097,666 B2 * | 8/2006 | Curtis | 623/38 |
| 7,108,722 B2 * | 9/2006 | Wagman | 623/38 |
| 7,135,022 B2 * | 11/2006 | Kosashvili et al. | 606/63 |
| 7,135,044 B2 * | 11/2006 | Bassik et al. | 623/22.42 |
| 7,175,664 B1 * | 2/2007 | Lakin | 623/19.14 |
| 7,198,642 B2 * | 4/2007 | Hazebrouck et al. | 623/16.11 |
| 7,217,060 B2 * | 5/2007 | Ingimarsson | 403/325 |
| 7,235,108 B2 * | 6/2007 | Carstens | 623/36 |
| 7,435,263 B2 * | 10/2008 | Barnett et al. | 623/19.12 |
| 7,445,638 B2 * | 11/2008 | Beguin et al. | 623/19.14 |
| 7,481,841 B2 * | 1/2009 | Hazebrouck et al. | 623/18.12 |
| 7,559,951 B2 * | 7/2009 | DiSilvestro et al. | 623/23.47 |
| 7,648,530 B2 * | 1/2010 | Habermeyer et al. | 623/19.11 |
| 7,722,678 B2 * | 5/2010 | Brown et al. | 623/32 |
| 7,753,915 B1 * | 7/2010 | Eksler et al. | 606/105 |
| 7,819,922 B2 * | 10/2010 | Sweeney | 623/17.16 |
| 7,955,357 B2 * | 6/2011 | Kiester | 606/258 |
| 8,048,167 B2 * | 11/2011 | Dietz et al. | 623/22.42 |
| 8,057,472 B2 * | 11/2011 | Walker et al. | 606/57 |
| 8,100,982 B2 * | 1/2012 | Heck et al. | 623/20.35 |
| 8,118,875 B2 * | 2/2012 | Rollet | 623/19.12 |
| 8,137,349 B2 * | 3/2012 | Soubeiran | 606/63 |
| 8,182,542 B2 * | 5/2012 | Ferko | 623/19.14 |
| 8,197,490 B2 * | 6/2012 | Pool et al. | 606/90 |
| 8,231,684 B2 * | 7/2012 | Mutchler et al. | 623/19.14 |
| 8,308,806 B2 * | 11/2012 | Grant et al. | 623/19.14 |
| 8,328,807 B2 * | 12/2012 | Brigido | 606/64 |
| 8,419,801 B2 * | 4/2013 | DiSilvestro et al. | 623/23.47 |
| 8,491,667 B2 * | 7/2013 | Dillingham | 623/32 |
| 8,858,641 B2 * | 10/2014 | Viscardi et al. | 623/19.11 |
| 8,906,102 B2 * | 12/2014 | Viscardi et al. | 623/19.11 |
| 2001/0053935 A1 * | 12/2001 | Hartdegen et al. | 623/19.12 |
| 2002/0116071 A1 * | 8/2002 | Slemker et al. | 623/36 |
| 2003/0032958 A1 * | 2/2003 | Soubeiran | 606/61 |
| 2003/0149486 A1 * | 8/2003 | Huebner | 623/19.11 |
| 2003/0171816 A1 * | 9/2003 | Scifert et al. | 623/22.12 |
| 2003/0195636 A1 * | 10/2003 | Coop | 623/36 |
| 2004/0030395 A1 * | 2/2004 | Blunn et al. | 623/18.12 |
| 2004/0102856 A1 * | 5/2004 | Hellberg | 623/33 |
| 2004/0122525 A1 * | 6/2004 | Daniels et al. | 623/22.42 |
| 2004/0138663 A1 * | 7/2004 | Kosashvili et al. | 606/62 |
| 2004/0193266 A1 * | 9/2004 | Meyer | 623/16.11 |
| 2004/0193267 A1 * | 9/2004 | Jones et al. | 623/16.11 |
| 2004/0193268 A1 * | 9/2004 | Hazebrouck | 623/16.11 |
| 2004/0220674 A1 * | 11/2004 | Pria | 623/19.12 |
| 2004/0230311 A1 * | 11/2004 | Cyprien et al. | 623/19.11 |
| 2005/0004679 A1 * | 1/2005 | Sederholm et al. | 623/22.42 |
| 2005/0071014 A1 * | 3/2005 | Barnett et al. | 623/19.14 |
| 2005/0125067 A1 * | 6/2005 | Sweeney | 623/19.14 |

(56) References Cited

U.S. PATENT DOCUMENTS

| | | | |
|---|---|---|---|
| 2005/0131550 A1* | 6/2005 | Coop | 623/36 |
| 2005/0216096 A1* | 9/2005 | Wagman | 623/38 |
| 2006/0004459 A1* | 1/2006 | Hazebrouck et al. | 623/18.12 |
| 2006/0069447 A1* | 3/2006 | DiSilvestro et al. | 623/23.16 |
| 2006/0142866 A1* | 6/2006 | Baratz et al. | 623/20.11 |
| 2006/0200249 A1* | 9/2006 | Beguin et al. | 623/19.14 |
| 2007/0043448 A1* | 2/2007 | Murray | 623/22.46 |
| 2007/0050039 A1* | 3/2007 | Dietz et al. | 623/19.13 |
| 2007/0112430 A1 | 5/2007 | Simmen et al. | |
| 2007/0244563 A1* | 10/2007 | Roche et al. | 623/19.12 |
| 2009/0076621 A1* | 3/2009 | Rollet | 623/23.45 |
| 2010/0228357 A1* | 9/2010 | Stauch | 623/23.47 |
| 2012/0109336 A1* | 5/2012 | Laghi | 623/33 |
| 2012/0116535 A1* | 5/2012 | Ratron et al. | 623/23.45 |
| 2013/0197656 A1* | 8/2013 | Conrad | 623/22.11 |
| 2013/0204376 A1* | 8/2013 | DiSilvestro et al. | 623/20.14 |

* cited by examiner

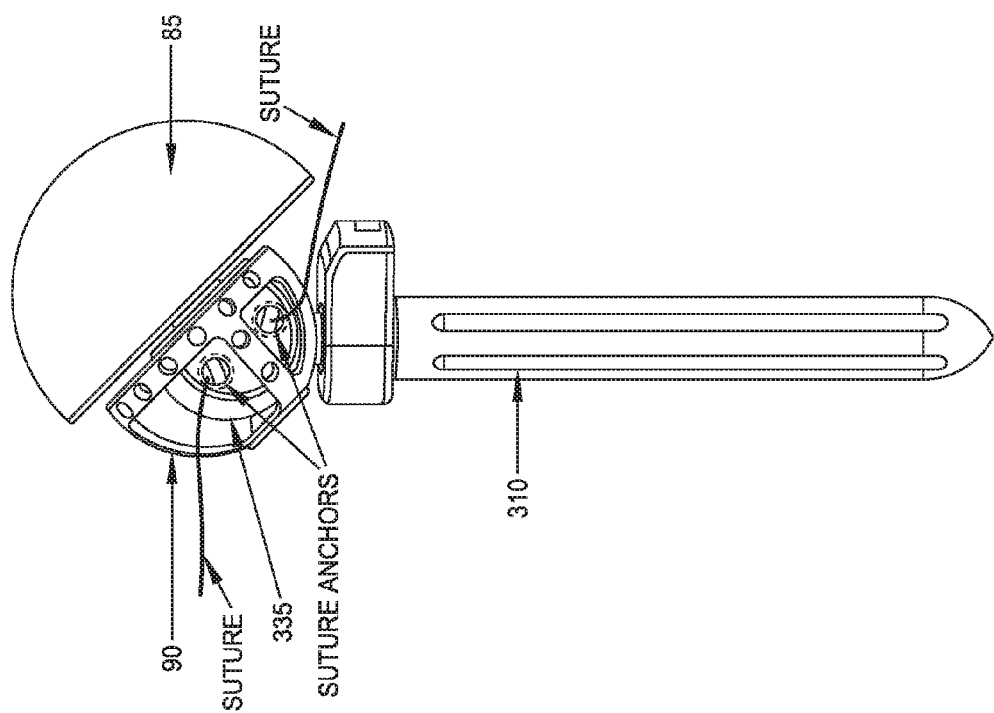

METHOD AND APPARATUS FOR RESTORING A JOINT, INCLUDING THE PROVISION AND USE OF A LONGITUDINALLY-ADJUSTABLE AND ROTATIONALLY-ADJUSTABLE JOINT PROSTHESIS

REFERENCE TO PENDING PRIOR PATENT APPLICATIONS

This patent application is a continuation of pending prior U.S. patent application Ser. No. 12/903,079, filed Oct. 12, 2010 by Barry T. Bickley et al. for METHOD AND APPARATUS FOR RESTORING A JOINT, COMPRISING THE PROVISION AND USE OF A LONGITUDINALLY-ADJUSTABLE AND ROTATIONALY-ADJUSTABLE JOINT PROSTHESIS, which in turn claims benefit of:

(i) prior U.S. Provisional Patent Application Ser. No. 61/278,782, filed Oct. 10, 2009 by Barry T. Bickley et al. for METHOD AND APPARATUS FOR RESTORING A JOINT, COMPRISING THE PROVISION AND USE OF A LONGITUDINALLY-ADJUSTABLE AND ROTATIONALLY-ADJUSTABLE JOINT PROSTHESIS; and (ii) prior U.S. Provisional Patent Application Ser. No. 61/368,424, filed Jul. 28, 2010 by Barry T. Bickley et al. for METHOD AND APPARATUS FOR RESTORING A JOINT, COMPRISING THE PROVISION AND USE OF A LONGITUDINALLY-ADJUSTABLE AND ROTATIONALY-ADJUSTABLE JOINT PROSTHESIS.

The above-identified patent applications are hereby incorporated herein by reference.

FIELD OF THE INVENTION

This invention relates to medical procedures and apparatus in general, and more particularly to medical procedures and apparatus for restoring a joint.

BACKGROUND OF THE INVENTION

Joint replacement surgery seeks to replace portions of a joint with prosthetic components so as to provide long-lasting function and pain-free mobility.

During joint replacement surgery, one or more of the operative elements of the joint are replaced by prosthetic components. More particularly, many joints (e.g., the hip, the shoulder, etc.) comprise a ball-and-socket construction. During total joint replacement surgery, the head of the bone which provides the ball is replaced by a prosthetic ball-and-stem, and the portion of the bone which provides the socket is replaced by a prosthetic cup, whereby to provide the prosthetic total joint. In a partial joint replacement surgery, only one of the operative elements of the joint may be replaced, e.g., the head of the bone which provides the ball.

The present invention is directed to situations where the head of the bone which provides the ball is replaced by a prosthetic ball-and-stem, or where the head of the bone which provides the socket is replaced by a prosthetic socket-and-stem, as will hereinafter be discussed in further detail. For convenience, the present invention will generally be discussed in the context of replacing the head of a bone with a prosthetic ball-and-stem, although it should be appreciated that the present invention is equally applicable to situations where the head of a bone is replaced by a prosthetic socket-and-stem.

In order to replace the head of a bone with a prosthetic ball-and-stem, the head of the bone is first distracted from its socket so as to expose the head of the bone. Then an osteotomy is performed so as to remove the neck and head of the bone from the remainder of the bone. This action also exposes the intramedullary canal (sometimes hereinafter referred to as "the bone canal") of the bone. Next, the proximal end of the bone canal is prepared to receive the stem of the prosthesis. More particularly, a rasp, reamer, broach, etc. is used to hollow out, clean and enlarge the proximal end of the bone canal so as to create an elongated cavity which will receive the stem of the prosthesis. Finally, the stem of the prosthesis is inserted into the bone canal so that the ball of the prosthesis is appropriately presented to the socket.

Typically, the ball of the prosthesis is manufactured separately from the stem of the prosthesis, with the ball component and the stem component being united at the time of use, although it is also possible to form the ball integral with the stem at the time of manufacture.

Furthermore, it should also be appreciated that, during the surgery itself, it is common to temporarily position a selected trial stem in the bone, attach a selected trial ball to the positioned trial stem, and then temporarily reduce the joint so as to confirm the joint reconstruction before the actual prosthetic stem is secured in position within the bone.

It will be appreciated that, when replacing the head of a bone with a prosthetic ball-and-stem, the surgeon must consider the position of the prosthetic ball relative to the socket, and that this must be done in both longitudinal and rotational terms. Specifically, the surgeon must consider (i) the longitudinal position of the prosthetic ball relative to the socket, and (ii) the rotational position of the prosthetic ball relative to the socket. This is necessary because, if either the longitudinal position or the rotational position of the prosthetic ball is "off" (i.e., mispositioned) vis-à-vis the socket, the ball will not seat properly in the socket and the prosthesis will not function as intended. As a practical matter, these positioning considerations require that a large inventory of prosthetic devices, of differing lengths and with differing angular orientations, must be maintained so that the prosthetic ball can be properly positioned in the patient. However, this is a costly requirement, and failures in inventory re-stocking can result in cancelled surgeries.

SUMMARY OF THE INVENTION

The present invention addresses the aforementioned problems associated with the prior art through the provision and use of a novel longitudinally-adjustable and rotationally-adjustable joint prosthesis.

More particularly, the present invention comprises a new joint prosthesis for replacing the ball of a ball-and-socket joint. This new joint prosthesis comprises (i) a sleeve which is adapted for disposition in the intramedullary canal of a bone, (ii) a center adapter which is adapted for disposition within the sleeve, and (iii) a ball mounted to the center adapter, wherein the disposition of the center adapter is adjustable, both longitudinally and rotationally, relative to the sleeve, so that the disposition of the ball is adjustable, both longitudinally and rotationally, relative to the socket.

Alternatively, the ball of the new prosthesis may be replaced by a socket, in order that the new prosthesis may replace the socket of a ball-and-socket joint. In this case, the disposition of the socket is adjustable, both longitudinally and rotationally, relative to the sleeve, so that the disposition of the socket is adjustable, both longitudinally and rotationally, relative to the ball.

In one preferred form of the present invention, there is provided a joint prosthesis for mounting in a first bone and presenting a prosthetic joint surface for engaging an opposing joint surface of a second bone, the joint prosthesis comprising:

a sleeve which is adapted for partial disposition in an opening formed in the first bone;

a center adapter which is adapted for disposition within the sleeve; and a prosthetic joint surface mounted to the center adapter;

wherein the disposition of the center adapter is adjustable, both longitudinally and rotationally, relative to the sleeve, so that the disposition of the prosthetic joint surface is adjustable, both longitudinally and rotationally, relative to the opposing joint surface of the second bone.

In another preferred form of the present invention, there is provided a method for restoring a joint, the method comprising:

providing a joint prosthesis for mounting in a first bone and presenting a prosthetic joint surface for engaging an opposing joint surface of a second bone, the joint prosthesis comprising:

a sleeve which is adapted for disposition in an opening formed in the first bone;

a center adapter which is adapted for partial disposition within the sleeve; and a prosthetic joint surface mounted to the center adapter;

wherein the disposition of the center adapter is adjustable, both longitudinally and rotationally, relative to the sleeve, so that the disposition of the prosthetic joint surface is adjustable, both longitudinally and rotationally, relative to the opposing joint surface of the second bone;

forming an opening in the first bone;

deploying a sleeve in the opening formed in the first bone;

positioning a center adapter partially within the sleeve;

adjusting the longitudinal and rotational position of the center adapter with respect to the sleeve; and securing the center adapter to the sleeve.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein:

FIGS. 30-36 are schematic views showing additional aspects of the present invention.

DETAILED DESCRIPTION OF THE INVENTION

Figure 1:
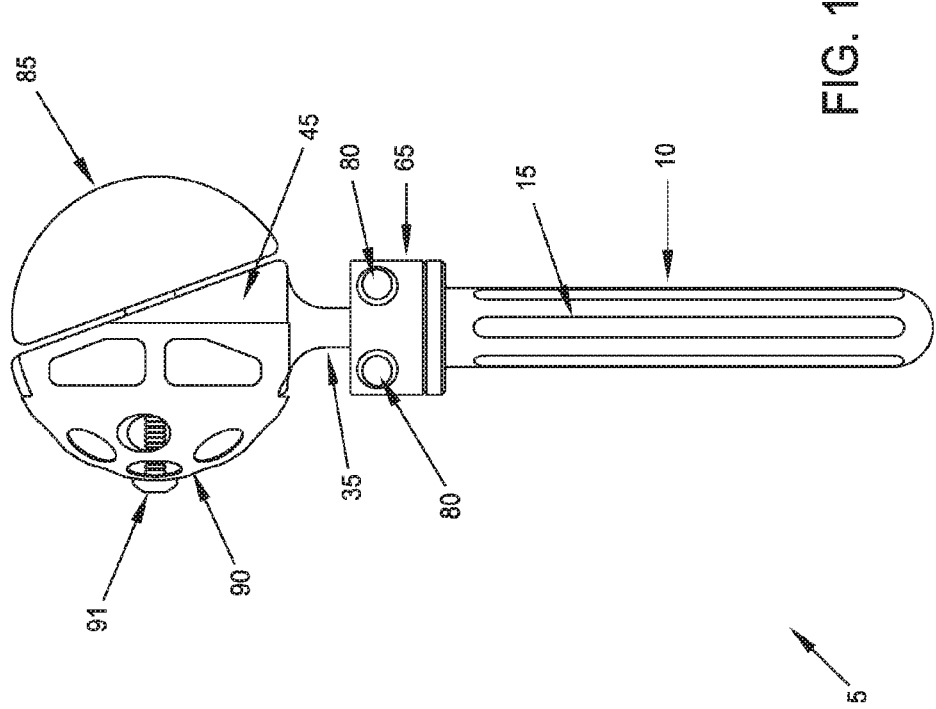
FIGS. 1-9 are schematic views showing various aspects of a first embodiment of the present invention.
Figure 2:
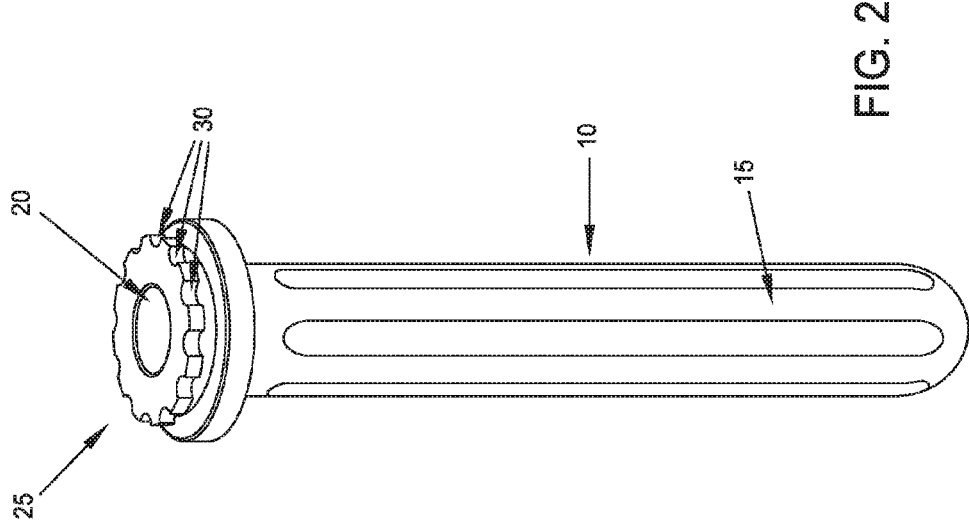
Figure 3:
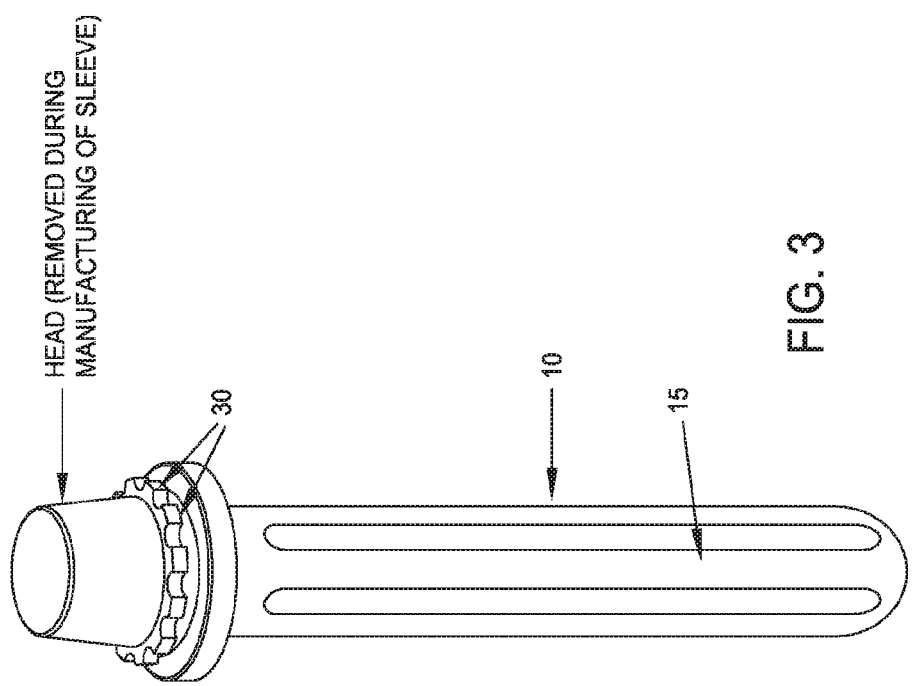
Figure 4:
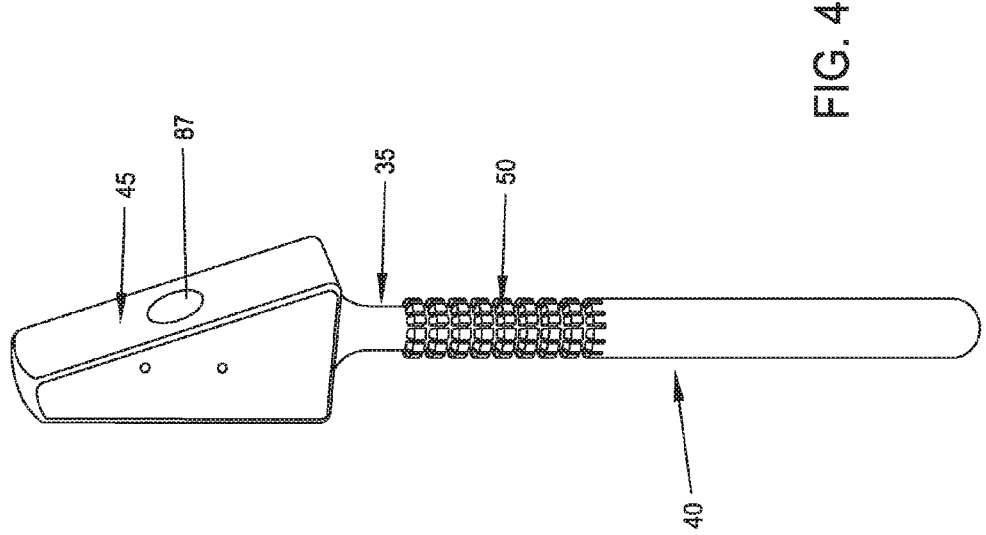
Figure 5:
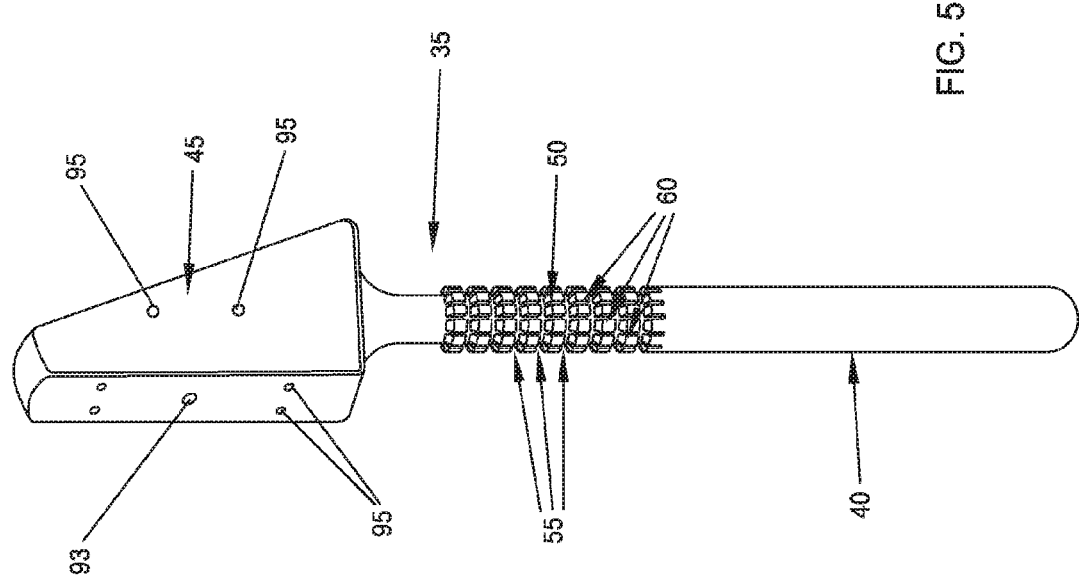
Figure 6:
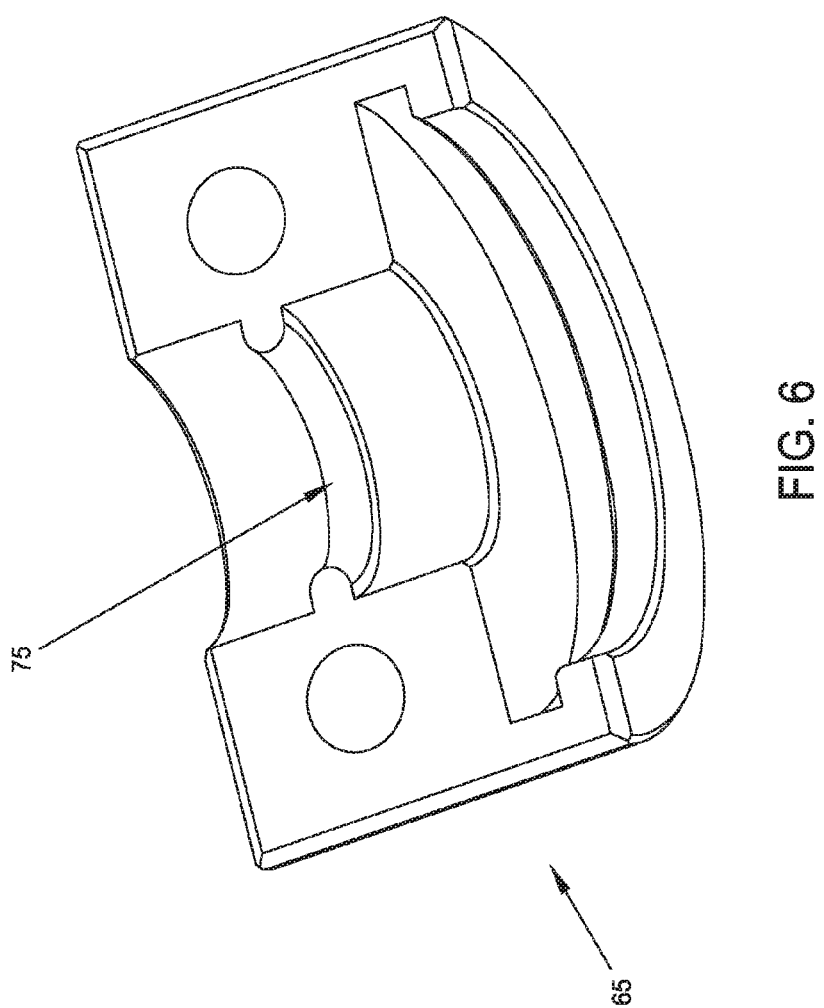
Figure 7:
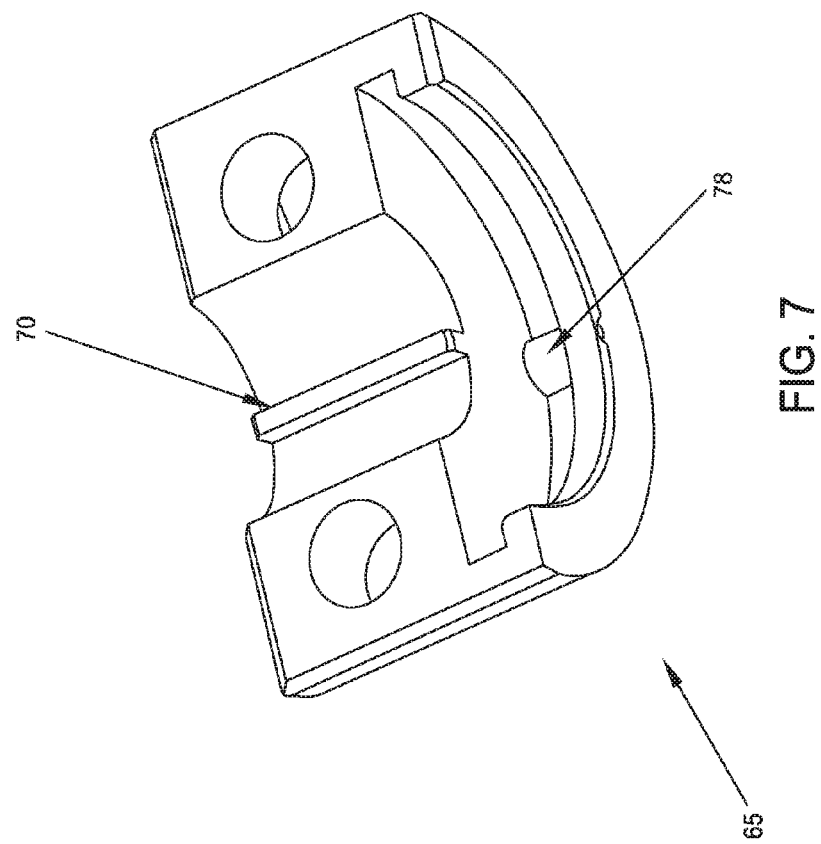
Figure 8:
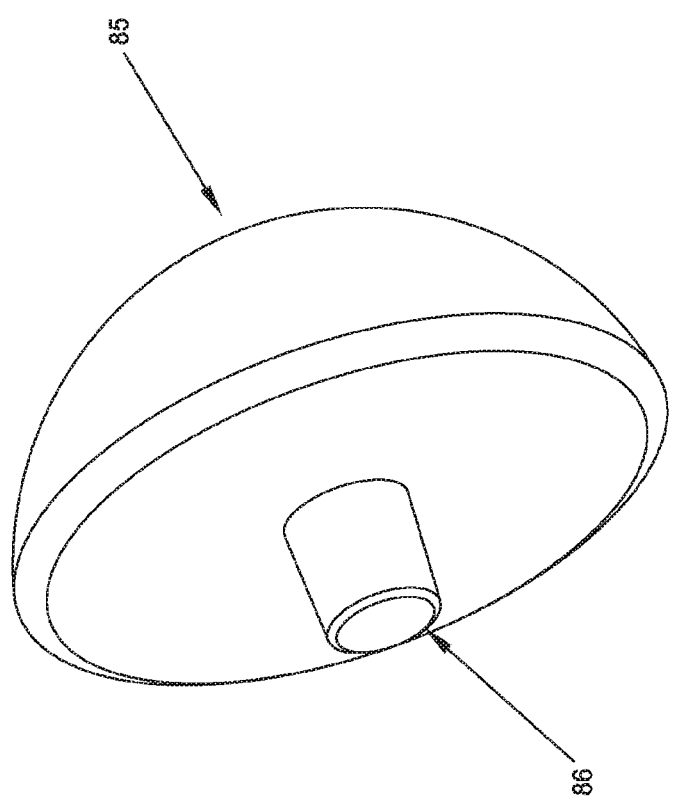
Figure 9:
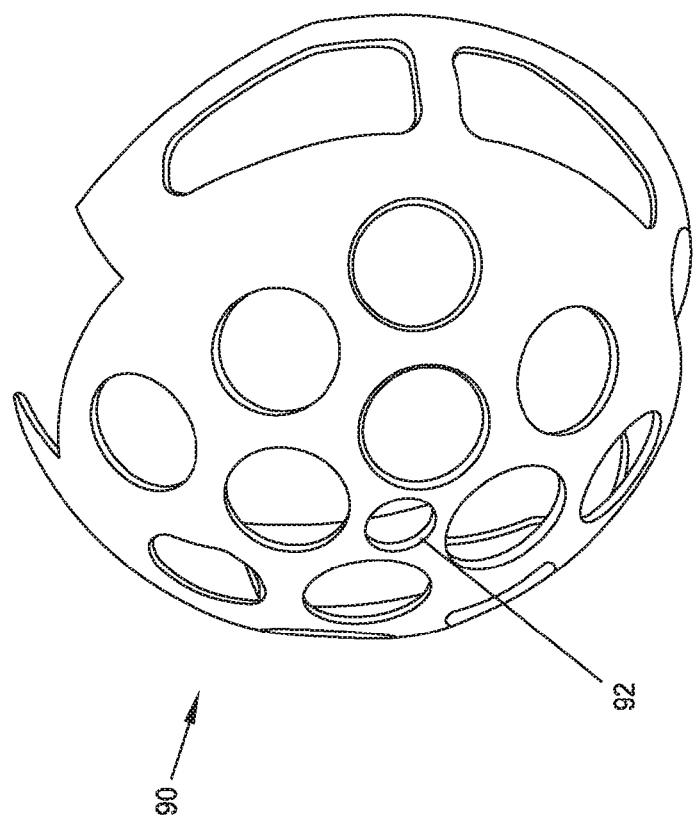
Figure 10:
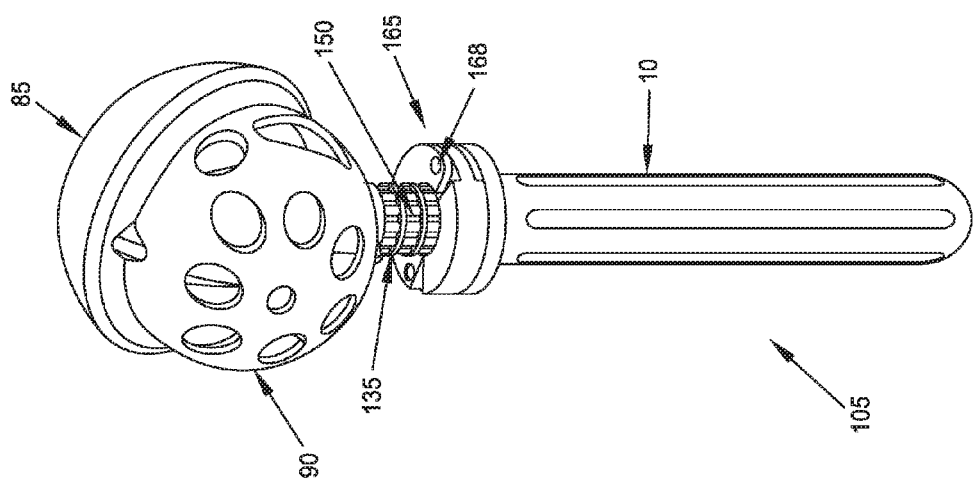
FIGS. 10-13 are schematic views showing various aspects of a second embodiment of the present invention.
Figure 11:
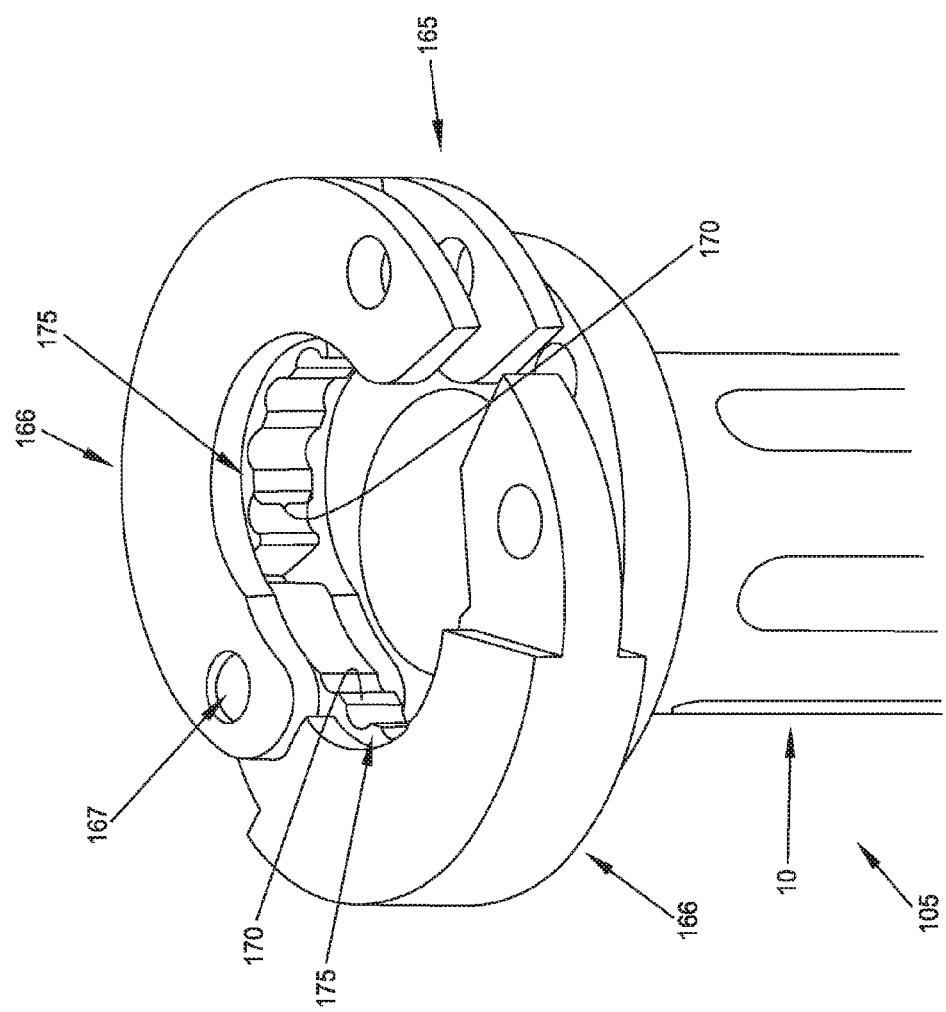
Figure 12:
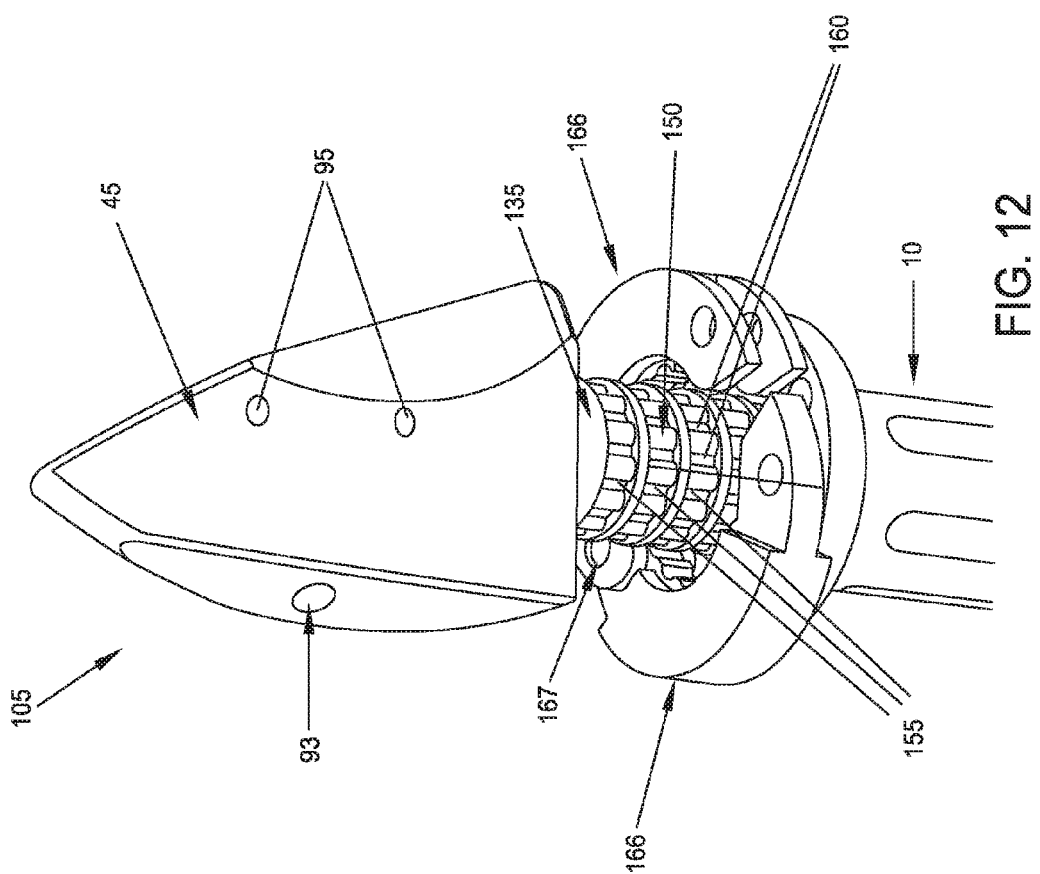
Figure 13:
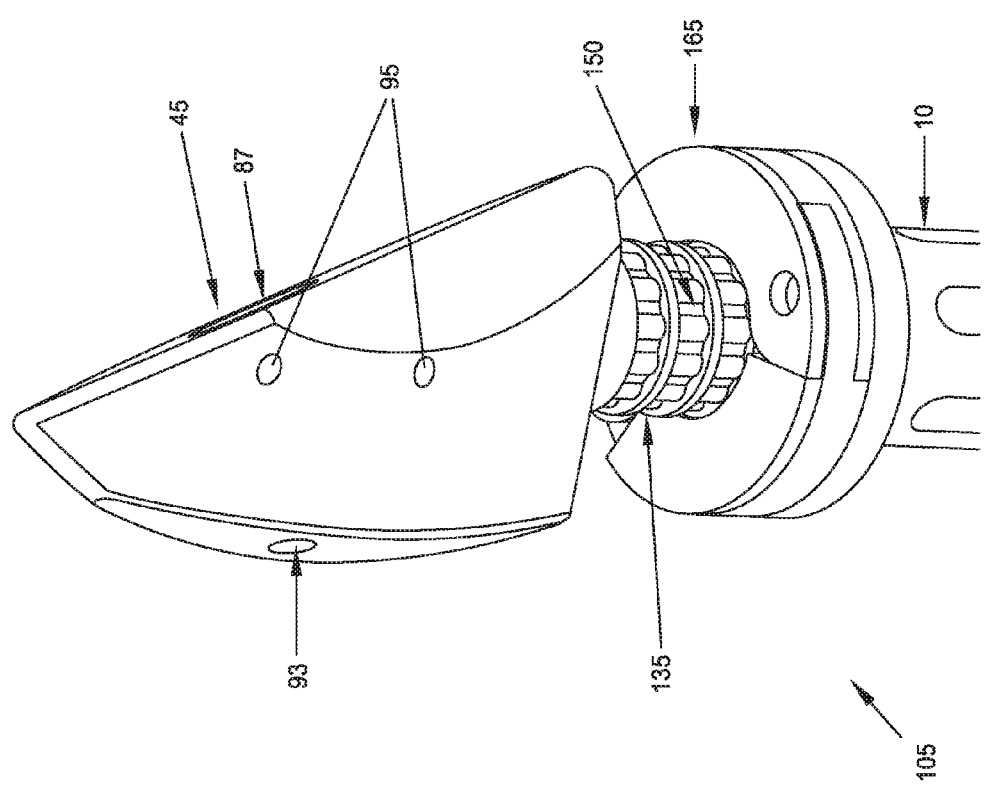
Figure 14:
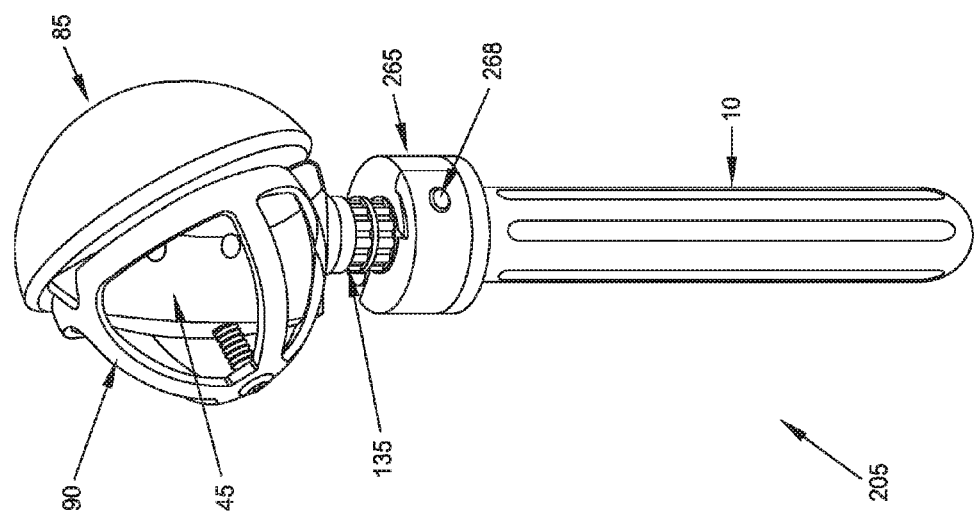
FIGS. 14-20 are schematic views showing various aspects of a third embodiment of the present invention.
Figure 15:
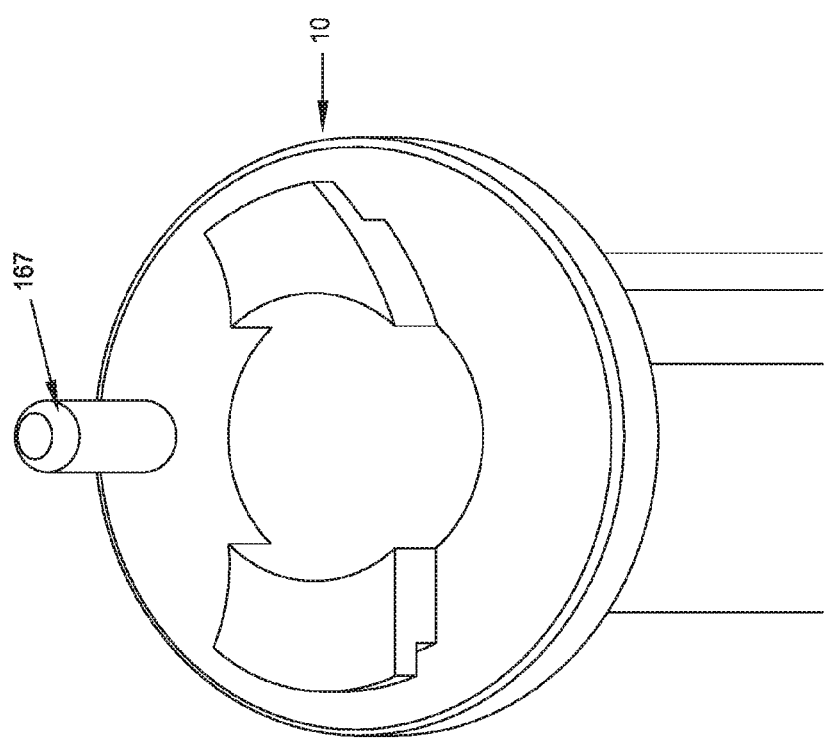
Figure 16:
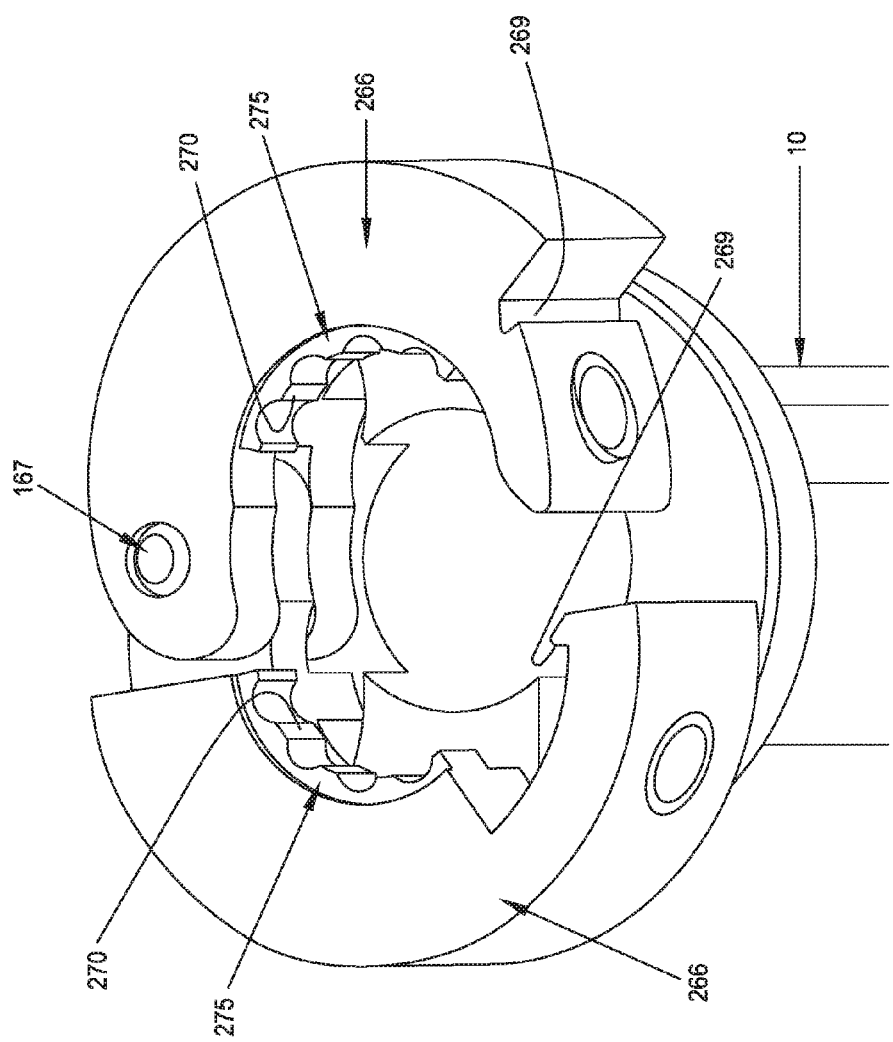
Figure 17:
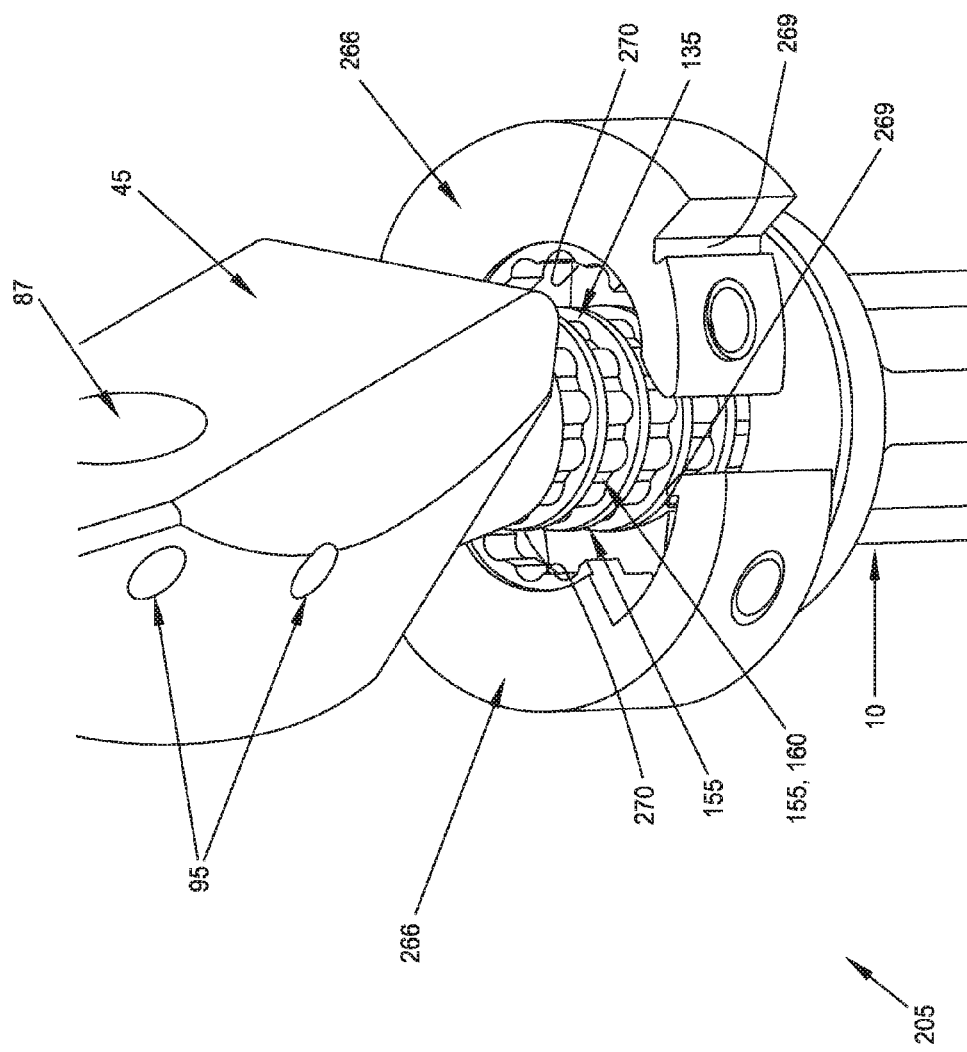
Figure 18:
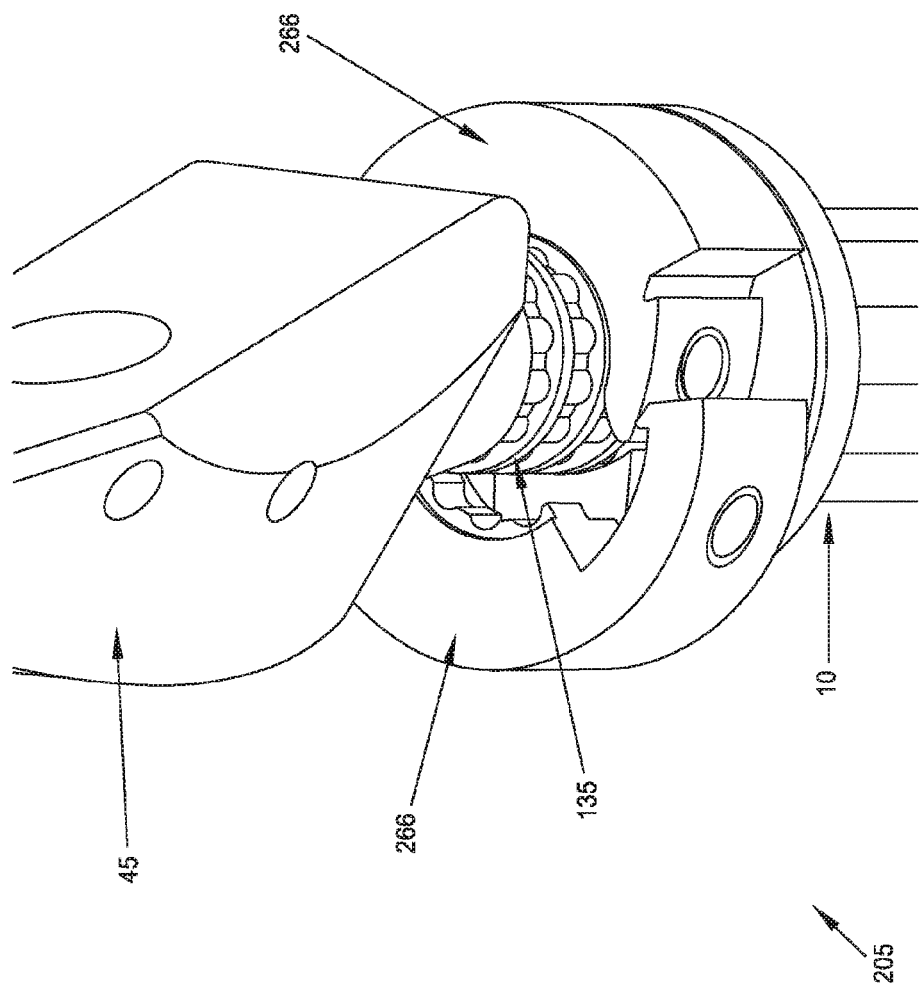
Figure 19:
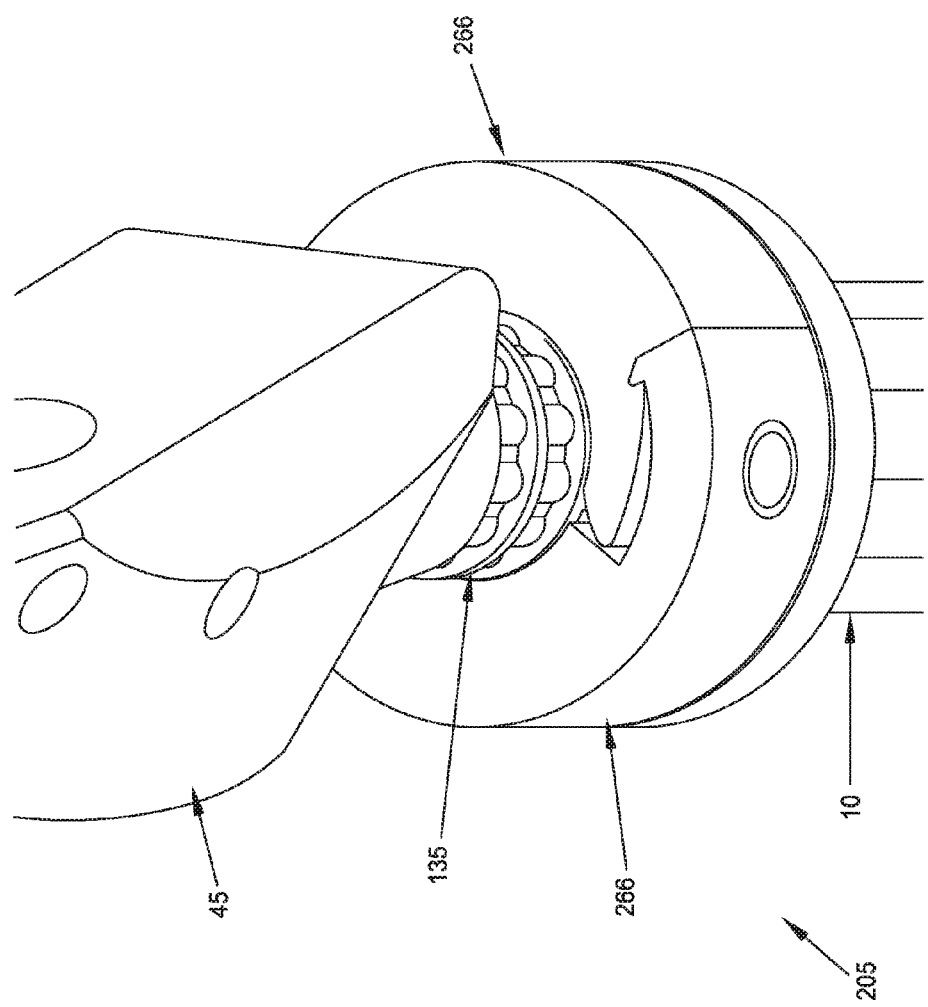
Figure 20:
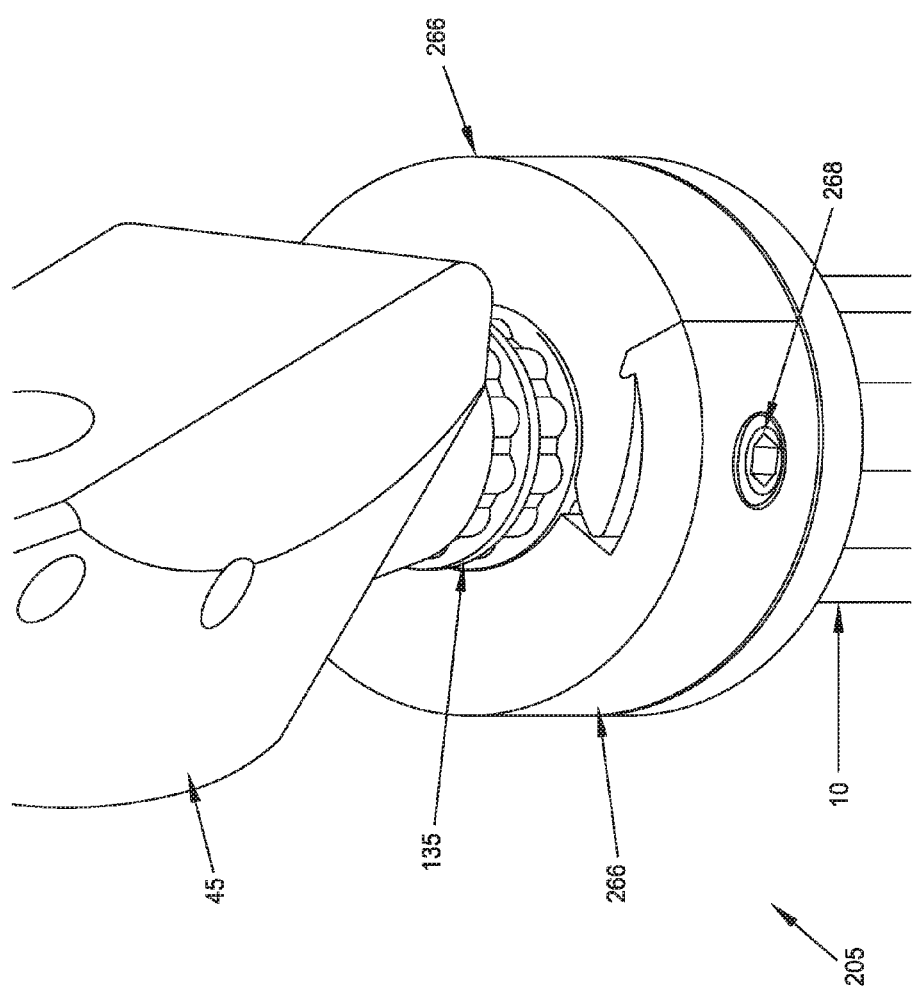
Figure 21:
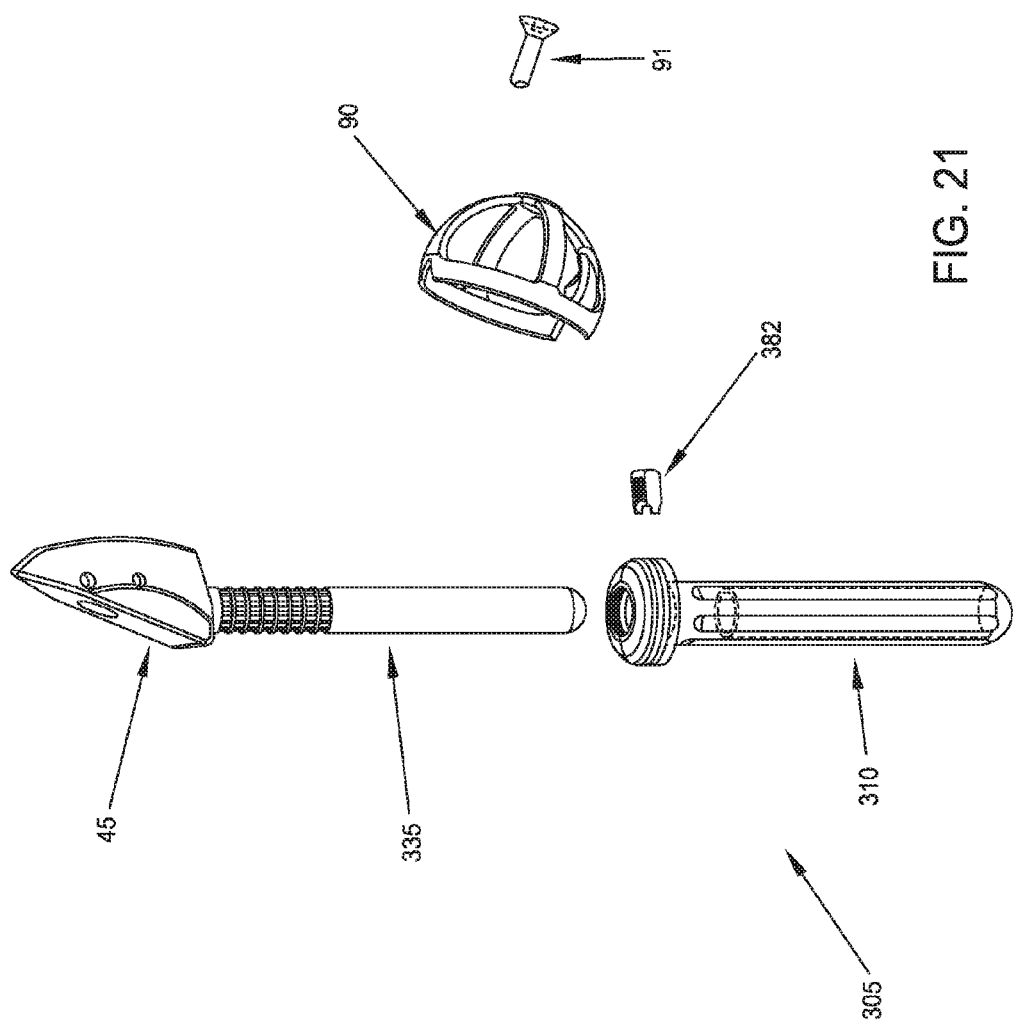
FIGS. 21-25 are schematic views showing various aspects of a fourth embodiment of the present invention.

The present invention is directed at a new joint prosthesis for replacing the ball of a ball-and-socket joint. This new joint prosthesis comprises (i) a sleeve which is adapted for disposition in the intramedullary canal of a bone, (ii) a center adapter which is adapted for disposition within the sleeve, and (iii) a ball mounted to the center adapter, wherein the disposition of the center adapter is adjustable, both longitudinally and rotationally, relative to the sleeve, so that the disposition of the ball is adjustable, both longitudinally and rotationally, relative to the socket.

Alternatively, the ball of the new prosthesis may be replaced by a socket, in order that the new prosthesis might replace the socket of a ball-and-socket joint. In this case, the disposition of the socket is adjustable, both longitudinally and rotationally, relative to the sleeve, so that the disposition of the socket is adjustable, both longitudinally and rotationally, relative to the ball.

Looking first at FIGS. 1-9, there is shown a new joint prosthesis 5 for replacing the ball of a ball-and-socket joint. Joint prosthesis 5 generally comprises a sleeve 10 (FIGS. 1-3) which is adapted for disposition in the intramedullary canal of a bone. Sleeve 10 generally comprises an elongated body 15 having a central lumen 20 (FIG. 2) formed therein, and terminating at its proximal end in a crown 25 having a plurality of peripheral detents 30 formed therein. A center adapter 35 (FIGS. 1, 4 and 5) is adapted for variable disposition within, and extension out of, central lumen 20 of sleeve 10. The disposition of center adapter 35 relative to sleeve 10 is adjustable, both longitudinally and rotationally. More particularly, center adapter 35 comprises an elongated shaft 40 terminating in a head 45. Elongated shaft 40 of center adapter 35 comprises a mount section 50 which comprises a plurality of horizontally-extending slots 55 and a plurality of longitudinally-extending slots 60. A two-piece collar 65 (FIGS. 6 and 7), having at least one longitudinally-extending internal rib 70 formed on at least one of the halves of the collar, and having at least one horizontally-extending internal rib 75 formed on at least one of the halves of the collar, and having at least one radially-projecting nib 78, is selectively fitted about crown 25 of sleeve 10 and mount section 50 of center adapter 35, as will hereinafter be discussed. Screws 80 (FIG. 1) are used to selectively hold the two halves of collar 65 together about crown 25 of sleeve 10 and mount section 50 of center adapter 35.

On account of the foregoing construction, when the two halves of collar 65 are loose, center adapter 35 is able to move both longitudinally and rotationally relative to collar 65, and collar 65 is able to move both longitudinally and rotationally relative to sleeve 10, since longitudinally-extending internal rib 70 of collar 65 will not project into a longitudinally-extending slot 60 of center adapter 35, and horizontally-extending internal rib 75 of collar 65 will not project into a horizontally-extending slot 55 of center adapter 35, and radially-projecting nib 78 of collar 65 will not project into a peripheral detent 30 of crown 25 of sleeve 10. However, when the two halves of collar 65 are tightened about crown 25 of sleeve 10 and mount section 50 of center adapter 35, the collar makes a binding fit with (i) center adapter 35, by virtue of the engagement of the collar's horizontally-extending internal rib 75 with one of the horizontally-extending slots 55 of the center adapter, and by virtue of the engagement of the collar's longitudinally-extending internal rib 70 with one of the longitudinally-extending slots 60 of the center adapter, and (ii) sleeve 10, by virtue of the engagement of the collar's radially-projecting nib 78 with one of the peripheral detents 30 on crown 25 of sleeve 10. In this way, by appropriately loosening collar 65 about crown 25 of sleeve 10 and mount section 50 of center adapter 35, the disposition of head 45 of center adapter 35 may be adjusted, both longitudinally and rotationally, relative to sleeve 10; and by appropriately tightening collar 65 about crown 25 of sleeve 10 and mount section 50 of center adapter 35, the disposition of head 45 of center adapter 35 may be fixed relative to sleeve 10.

Ball 85 (FIG. 8) is adapted to be secured to head 45 of center adapter 35. By way of example but not limitation, ball 85 may include a stem 86 for positioning in a recess 87 formed in head 45.

Accordingly, it will be appreciated that, in view of the foregoing construction, the disposition of ball 85 can be adjusted, both longitudinally and rotationally, relative to sleeve 10, and hence the disposition of ball 85 may be adjusted, both longitudinally and rotationally, relative to a bone in which sleeve 10 is disposed. In this way, the present invention provides a new joint prosthesis which permits the disposition of the ball to be adjusted, both longitudinally and rotationally, relative to a socket.

If desired, a cage 90 (FIG. 9) may be mounted to the opposing side of head 45 (FIG. 1). By way of example but not limitation, a screw 91 (FIG. 1) received in a hole 92 (FIG. 9) in cage 95 and a hole 93 (FIG. 5) in head 45 may be used to secure cage 90 to head 45. The provision of a cage on the prosthesis, preferably diametrically opposed to the ball, permits soft tissue or bone to be secured to the prosthesis, e.g., with sutures.

Also, if desired, openings 95 (FIG. 5) may be formed in center adapter 35 (e.g., in head 45), in collar 65 and/or in cage 90, so as to receive a suture or a suture anchor, or like fastening element, whereby to permit soft tissue and/or bone to be secured to the joint prosthesis.

In use, sleeve 10 (preferably having collar 65 loosely secured thereto) is disposed in the intramedullary canal of a bone, center adapter 35 (preferably having ball 85 secured thereto) is inserted into central lumen 20 of the sleeve and is moved longitudinally and rotationally as needed so as to present the ball for proper seating in the socket, and then collar 65 is tightened (e.g., with screws 80) so as to secure center adapter 35, and hence ball 85, in the desired longitudinal and rotational position relative to sleeve 10, and hence in the desired longitudinal and rotational position relative to the socket.

Looking next at FIGS. 10-13, there is shown an alternative form of the new joint prosthesis for replacing the ball of a ball-and-socket joint. The new joint prosthesis 105 of FIGS. 10-13 is generally similar to the joint prosthesis 5 shown in FIGS. 1-9, except that (i) center adapter 35 of FIGS. 1-9 is replaced by the center adapter 135 shown in FIGS. 10-13, and (ii) collar 65 of FIGS. 1-9 is replaced by the hinged collar 165 shown in FIGS. 10-13.

More particularly, the center adapter 135 of FIGS. 10-13 is substantially the same as the center adapter 35 of FIGS. 1-9, except that the mount section 50 of center adapter 35 is replaced by the mount section 150 of center adapter 135. In mount section 150, the horizontally-extending slots 155 (FIG. 12) and the longitudinally-extending slots 160 are effectively superimposed on one another, in the manner shown in FIG. 12.

In addition, the hinged collar 165 of FIGS. 10-13 comprises two halves 166 which are hinged together by a pivot pin 167 rising out of sleeve 10. A locking pin 168 (FIG. 10) is used to selectively lock the two halves 166 together. At least one, and preferably both, of the two halves 166 includes longitudinally-extending internal ribs 170 which are formed on a horizontally-extending internal rib 175. Thus, with the construction shown in FIGS. 10-13, the longitudinally-extending internal ribs 170 are effectively superimposed on the horizontally-extending internal ribs 175.

It will be appreciated that, in this form of the invention, when the two halves 166 of collar 165 are separated from one another, the horizontally-extending internal ribs 175 and the longitudinally-extending internal ribs 170 of collar 165 will be separated from the horizontally-extending slots 155 and the longitudinally-extending slots 160 of center adapter 135, and the center adapter will be free to move longitudinally and rotationally relative to the collar, and hence longitudinally and rotationally relative to the sleeve 10 to which the collar is mounted.

It will also be appreciated that, in this form of the invention, when the two halves 166 of collar 165 are locked together with locking pin 168, horizontally-extending internal ribs 175 of collar 165 will seat in horizontally-extending slots 155 in center adapter 135, and longitudinally-extending internal ribs 170 of collar 165 will seat in longitudinally-extending slots 160 of center adapter 135, whereby to lock center adapter 135 longitudinally and rotationally relative to the collar, and hence to the sleeve 10 to which the collar is mounted.

Accordingly, in view of the foregoing construction, the disposition of ball 85 can be adjusted, both longitudinally and rotationally, relative to sleeve 10, and hence may be adjusted, both longitudinally and rotationally, relative to a bone in which sleeve 10 is disposed. In this way, the present invention provides a new joint prosthesis which permits the disposition of the ball to be adjusted, both longitudinally and rotationally, relative to a socket.

Looking next at FIGS. 14-20, there is shown another alternative form of the new joint prosthesis for replacing the ball of a ball-and-socket joint. The new joint prosthesis 205 of FIGS. 14-20 is generally similar to the joint prosthesis 105 shown in FIGS. 10-13, except that the collar 165 used in the construction of FIGS. 10-13 is replaced by a latched collar 265 as shown in FIGS. 14-20.

More particularly, latched collar 265 comprises two halves 266 pivotally mounted to the pivot pin 167 of sleeve 10. The two halves 266 of latched collar 265 are substantially the same as the two halves 166 of hinged collar 165, except that the two halves 266 of latched collar 265 also each comprise a latch mechanism 269 at its free end. Thus, at least one, and preferably both, of the two halves 266 includes a horizontally-extending internal rib 275 carrying a plurality of longitudinally-extending internal ribs 270 thereon. Accordingly, it will be appreciated that with the construction shown in FIGS. 14-20, the longitudinally-extending internal ribs 270 are again effectively superimposed on the horizontally-extending internal ribs 275. Latch mechanisms 269 engage one another when the two halves 266 are brought together so that the two halves can catch to one another. A locking pin 268 (FIG. 14) may be used to secure the two halves in their closed condition.

It will be appreciated that, in this form of the invention, when the two halves 266 of collar 265 are separated from one another, the horizontally-extending internal ribs 275 and the longitudinally-extending internal ribs 270 of collar 265 will be separated from the horizontally-extending slots 155 and the longitudinally-extending slots 160 of center adapter 135, and the center adapter will be free to move longitudinally and rotationally relative to the collar, and hence longitudinally and rotationally relative to the sleeve 10 to which the collar is mounted.

It will also be appreciated that, in this form of the invention, when the two halves 266 of collar 265 are locked together with locking pin 268, horizontally-extending internal ribs 275 of collar 265 will seat in horizontally-extending slots 155 in center adapter 135, and longitudinally-extending internal ribs 270 of collar 265 will seat in longitudinally-extending slots 160 of center adapter 135, whereby to lock center adapter 135 longitudinally and rotationally relative to the collar, and hence to the sleeve 10 to which the collar is mounted.

Accordingly, in view of the foregoing construction, the disposition of ball 85 can be adjusted, both longitudinally and rotationally, relative to sleeve 10, and hence may be adjusted, both longitudinally and rotationally, relative to a bone in which sleeve 10 is disposed. In this way, the present invention provides a new joint prosthesis which permits the disposition of the ball to be adjusted, both longitudinally and rotationally, relative to a socket.

Looking next at FIGS. 21-25, there is shown another alternative form of the new joint prosthesis for replacing the ball of a ball-and-socket joint. The new joint prosthesis 305 of FIGS. 21-25 is generally similar to the joint prosthesis 205 shown in FIGS. 14-20, except as will hereinafter be discussed.

More particularly, with the joint prosthesis 305 of FIGS. 21-25, collar 265 is omitted and the sleeve 10 of FIGS. 14-20 is replaced by a new sleeve 310. Sleeve 310 comprises a plurality of horizontally-extending internal ribs 375 (FIGS. 23 and 25) which are separated from one another by bands of recessed wall 376. Each of the horizontally-extending external ribs 375 carries a plurality of longitudinally-extending internal ribs 370 (FIG. 23) thereon. A threaded keyway 377 (FIG. 23) is formed in the side wall of sleeve 310. Threaded keyway 377 communicates with central lumen 320 of sleeve 310.

Figure 22:
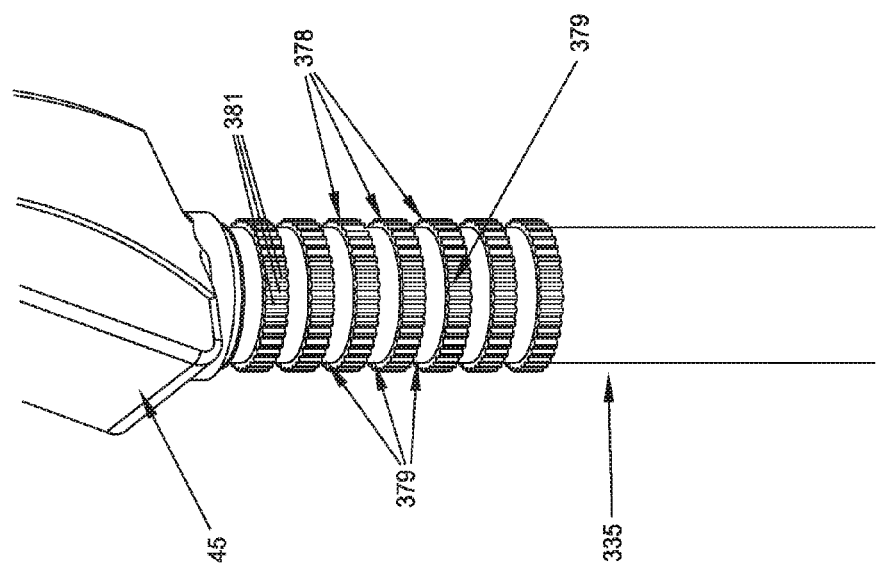
Figure 23:
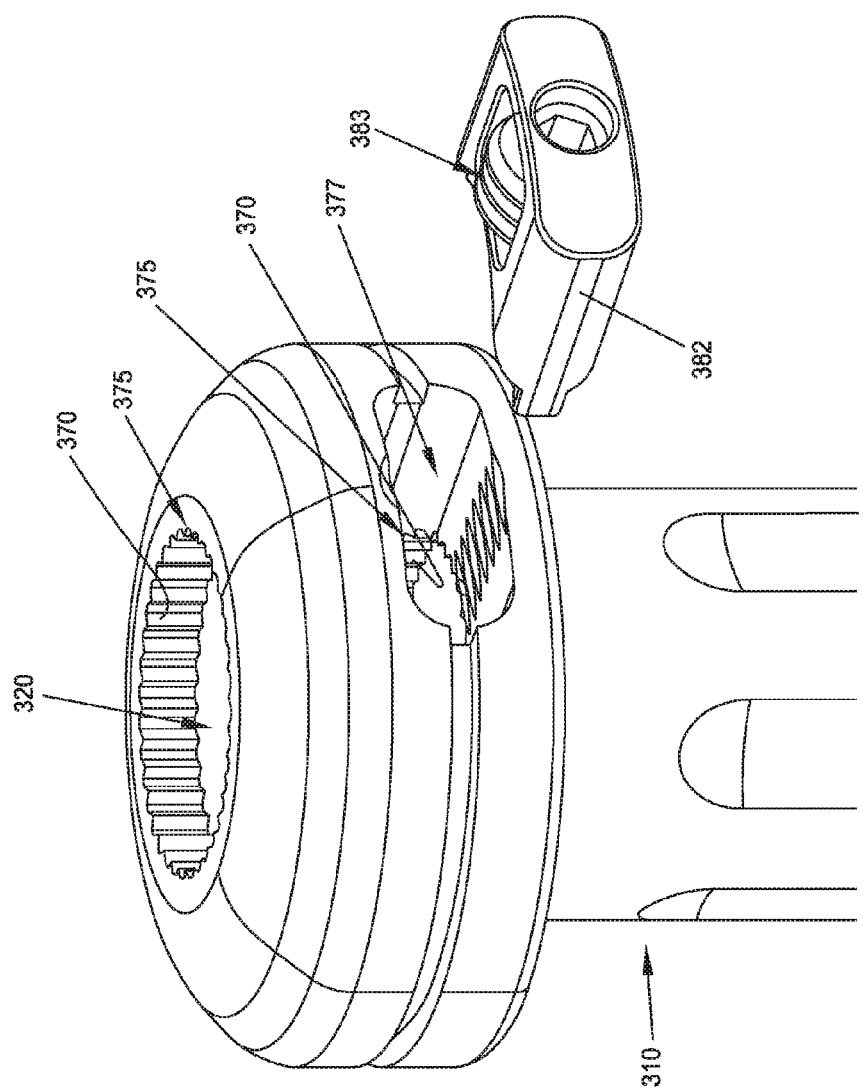
Figure 24:
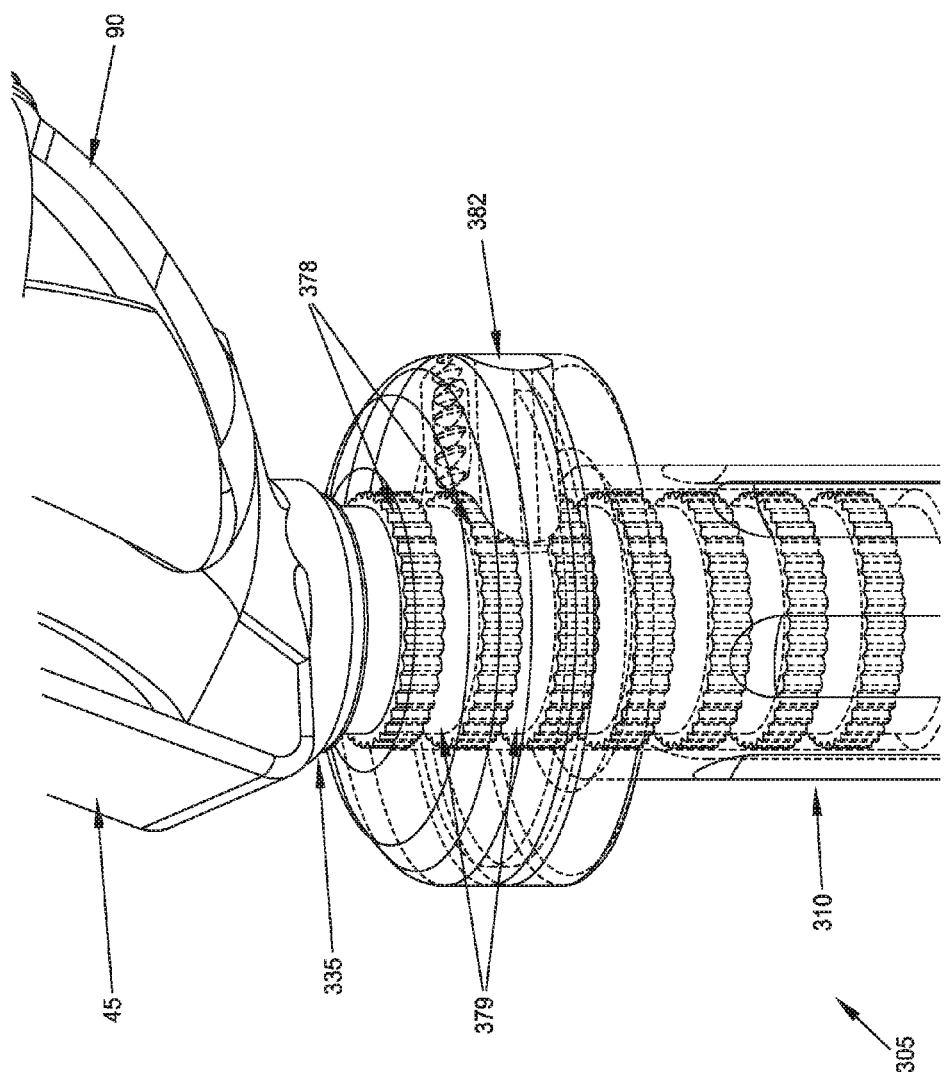

In this form of the invention, the center adapter 135 of FIGS. 14-20 is replaced by a new center adapter 335 (FIG. 22). Center adapter 335 is substantially the same as the center adapter 135 of FIGS. 14-20, except that center adapter 335 comprises a plurality of horizontally-extending ribs 378 which are separated from one another by bands of recessed wall 379. Thus, the bands of recessed wall 379 essentially comprise horizontally-extending slots in center adapter 335. Each of the horizontally-extending ribs 378 carries a plurality of longitudinally-extending slots 381 (FIG. 23) thereon.

And in this form of the invention, there is also provided a key lock 382 which is radially movable along threaded keyway 377 via a screw 383.

Figure 25:
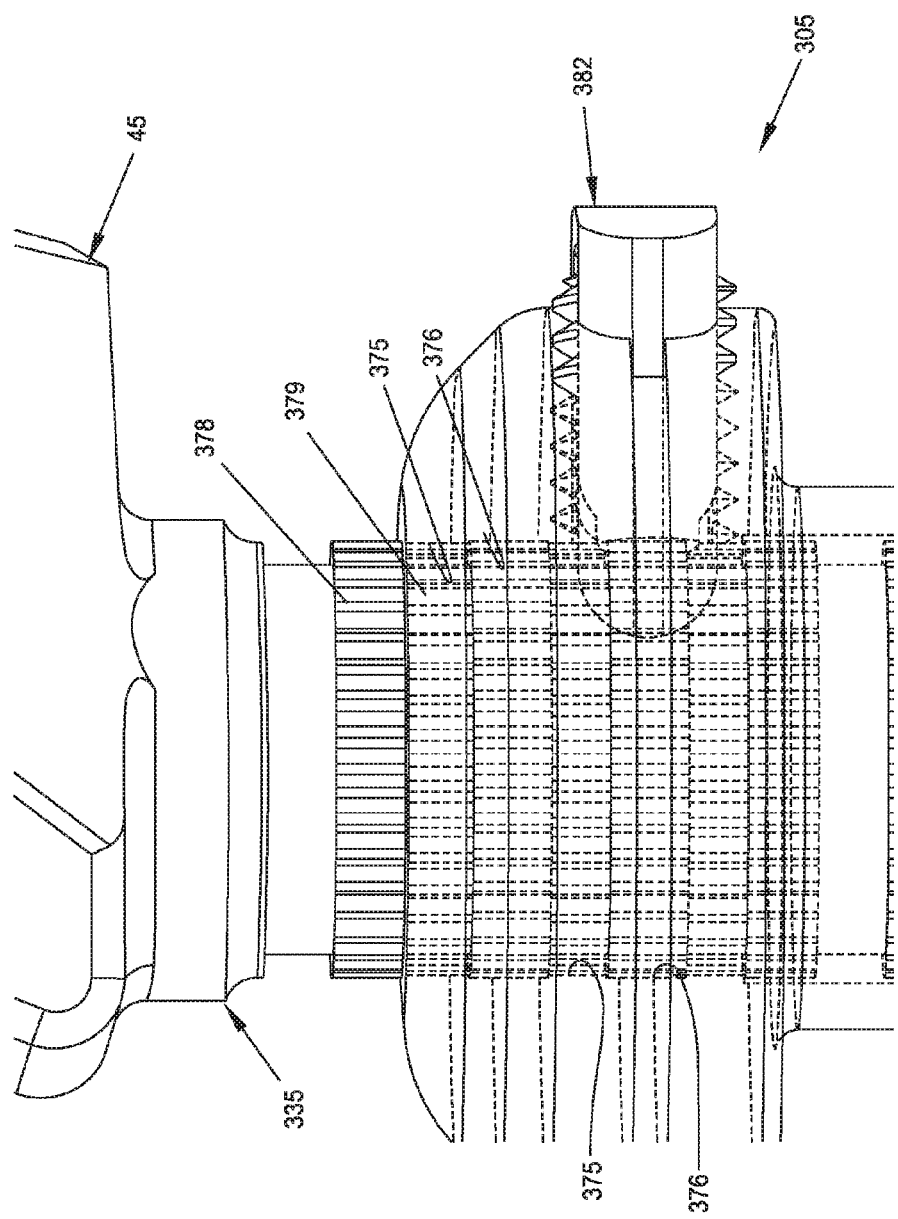

As a result of this construction, and looking now at FIG. 25, when it is desirable to adjust the position (either longitudinally or rotationally) of center adapter 335 relative to sleeve 310, key lock 382 is backed out along threaded keyway 377, center adapter 335 is moved longitudinally relative to sleeve 310 as desired and then, in order to accommodate rotational adjustment, center adapter 335 is moved slightly longitudinally if and as needed so as to align the horizontally-extending ribs 378 of center adapter 335 with the bands of recessed wall 376 of sleeve 310 and so as to align the bands of recessed wall 379 of center adapter 335 with the horizontally-extending ribs of 375 of sleeve 310, whereupon the rotational position of the center adapter may be adjusted vis-à-vis the sleeve. Then center adapter 335 is moved longitudinally slightly, so that the horizontally-extending ribs 378 of the center adapter are aligned with the horizontally-extending ribs 375 of sleeve 310, with the longitudinally-extending internal ribs 370 of sleeve 310 being received within the longitudinally-extending slots 381 of center adapter 335. This action locks center adapter 335 against rotational movement relative to sleeve 310. Then key lock 382 is advanced along threaded keyway 377 via screw 383 until the inner end of the key lock engages one of the bands of recessed wall 379 in center adapter 335. In other words, the distal end of key lock 382 projects into the horizontally-extending slot formed in the center adapter by the band of recessed wall 379 disposed between two adjacent horizontally-extending ribs 378. This action locks center adapter 335 against longitudinal movement relative to sleeve 310, since the inner end of key lock 382 engages the two horizontally-extending ribs 378 of center adapter 335 which are disposed on either side of key lock.

Accordingly, it will be appreciated that, in view of the foregoing construction, the disposition of ball 85 can be adjusted, both longitudinally and rotationally, relative to sleeve 10, and hence the disposition of ball 85 may be adjusted, both longitudinally and rotationally, relative to a bone in which sleeve 10 is disposed. In this way, the present invention provides a new joint prosthesis which permits the disposition of the ball to be adjusted, both longitudinally and rotationally, relative to a socket.

It is also possible for the prosthesis to provide a socket, rather than a ball, at the free end of the center adapter.

Figure 26:
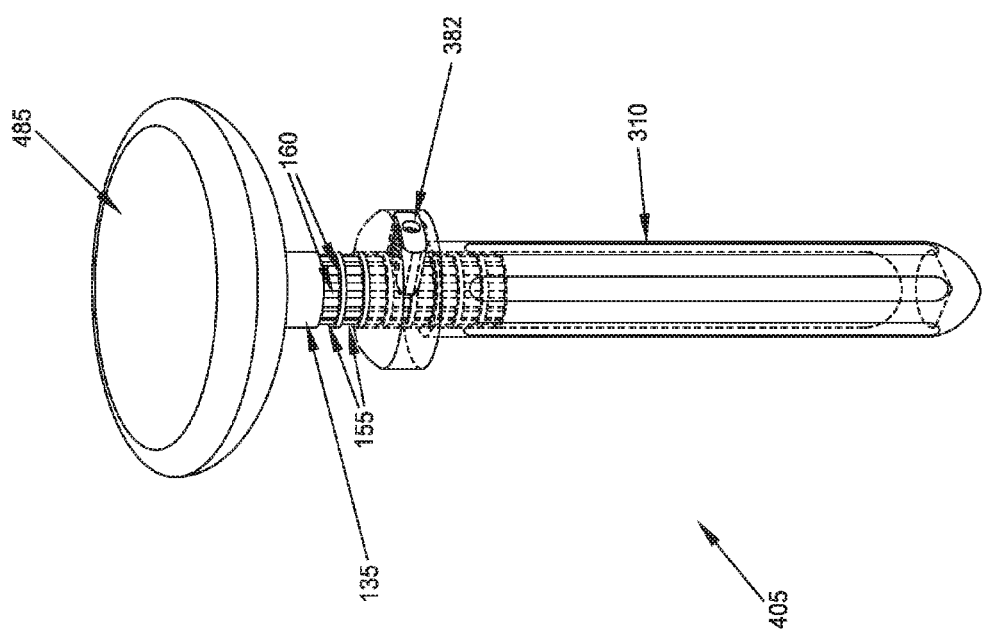
FIG. 26 is a schematic views showing various aspects of a fifth embodiment of the present invention.

Thus, for example, FIG. 26 shows a novel joint prosthesis 405 which provides a socket 485, rather than the head 45 and ball 85, at the proximal end of center adapter 135. In this respect it should also be appreciated that the joint prosthesis 405 shown in FIG. 26 comprises the aforementioned center adapter 135 (except modified to include socket 485) in combination with the aforementioned sleeve 310, with key lock 382 being used to selectively lock center adapter 135 to sleeve 310. Thus, in this form of the invention, rotational locking is provided by virtue of the disposition of the longitudinally-extending internal ribs 370 in the longitudinally-extending slots 160 of center adapter 135, and longitudinal locking is provided by virtue of the disposition of the toe of key lock 382 in the horizontally-extending slots 155 in center adapter 135.

Figure 27:
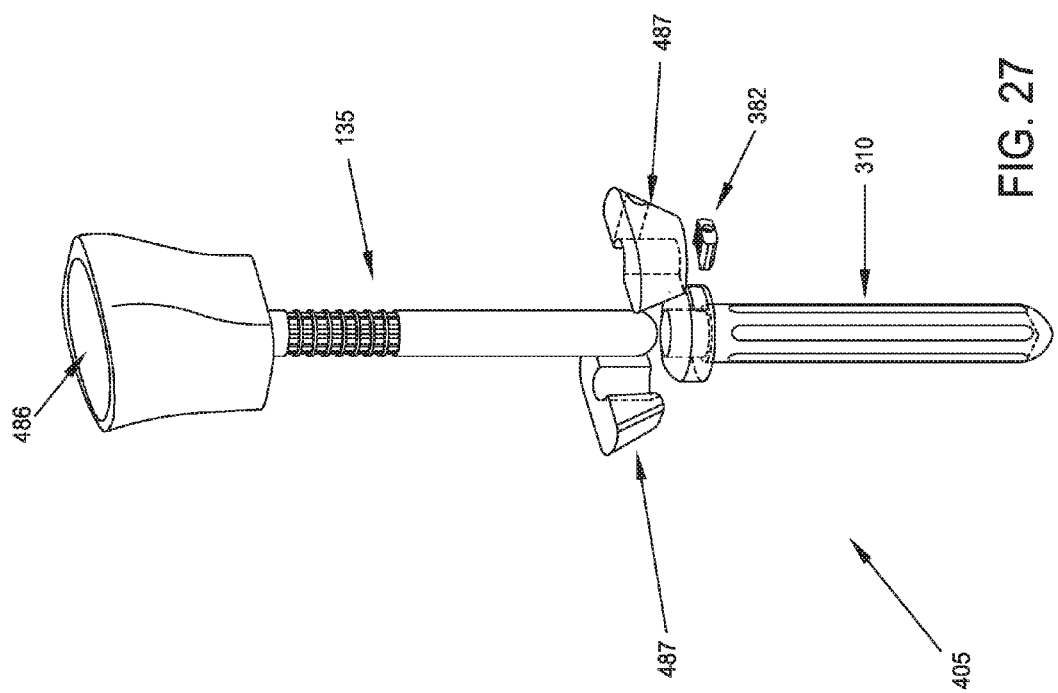
FIGS. 27-29 are schematic views showing various aspects of a sixth embodiment of the present invention.
Figure 28:
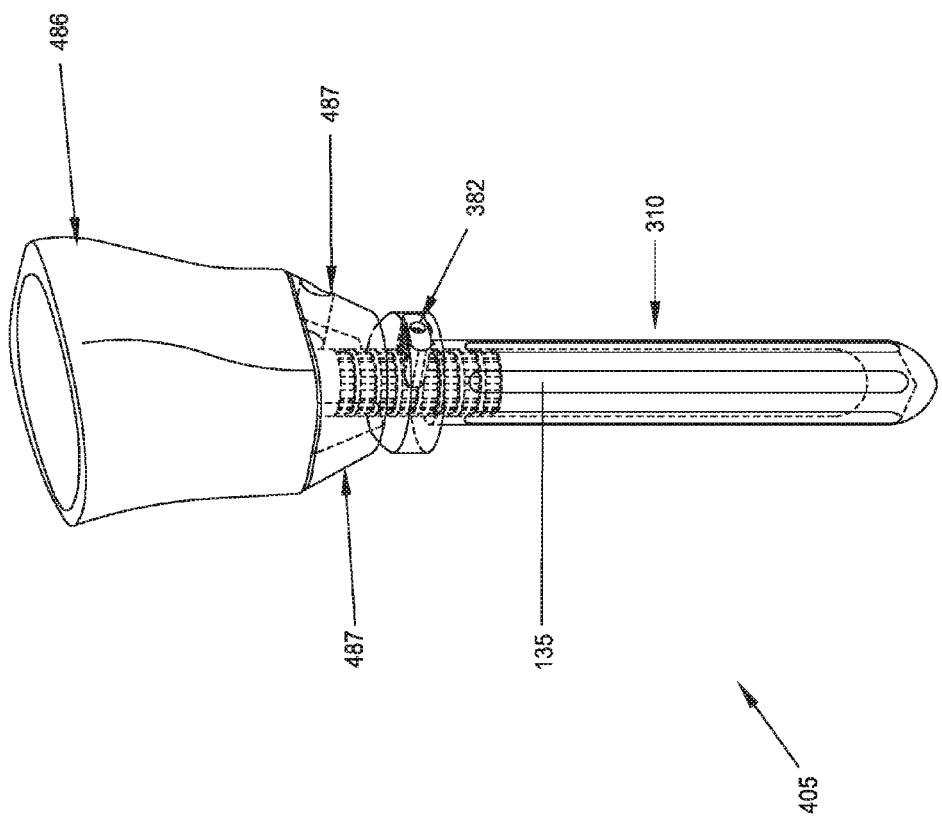
Figure 29:
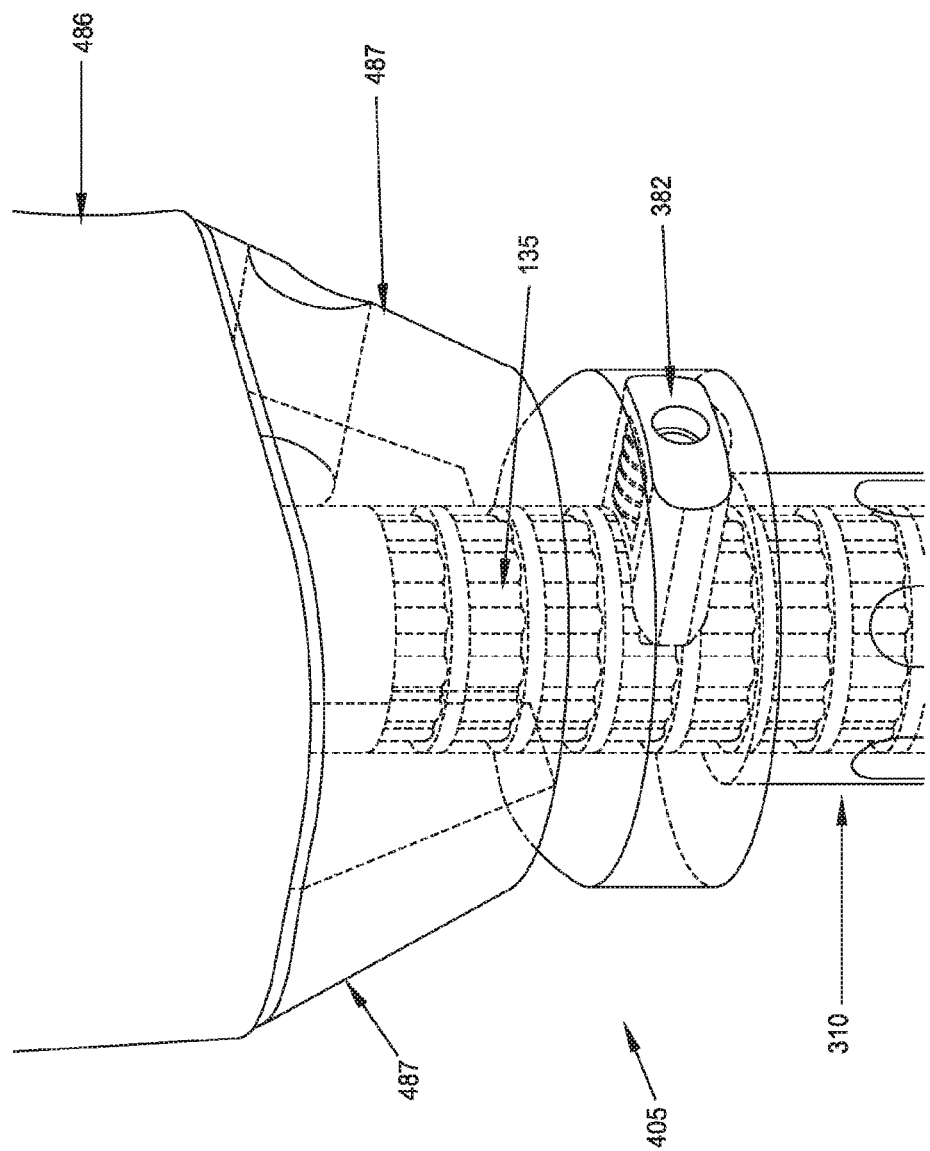

By way of further example, FIGS. 27-29 show another novel joint prosthesis 405 which provides an alternative form of socket 486 at the distal end of center adapter 135. If desired, a support collar 487 may be provided between the top of sleeve 310 and the bottom of socket 486 so as to provide increased support for the socket element. Furthermore, if desired, this support collar may be formed in two separate halves, united at the time of use, so as to facilitate deployment at the surgical site.

EXAMPLE

Intended Use

The device and its associated method of use provide, in one exemplary use, a proximal humerus replacement prosthesis. The purpose of this exemplary device is to replace the humeral head articular surface when the bone is damaged. These situations would include fractures and/or dislocation, aseptic necrosis or various forms of arthritis such as osteoarthritis, rheumatoid arthritis or post traumatic arthritis, failed joint replacement or any other situation where arthrodesis or other reconstructive procedures would not be expected to give a satisfactory outcome.

Design

The exemplary shoulder prosthesis system includes prosthetic components and instrumentation for the implantation of a modular proximal humerus replacement. Some unique aspects of this system, among others, are that it allows adjustment of the final prosthesis in height and rotation (version), i.e., longitudinally and rotationally, as well as having special features to facilitate re-attachment of bone and soft tissue if that is desired. The height and version (i.e., the longitudinal disposition and the rotational disposition) of the humeral prosthesis are critical factors in performing a shoulder replacement procedure. These variables are particularly difficult to measure in cases of fracture or other situations of distorted anatomy such as aseptic necrosis or fracture malunion. These variables are normally measured through a trialing process. However, in the setting of a fracture, it is very difficult to secure the trial to the shaft of the humerus. Therefore the trial moves and shifts easily, making measurements very inaccurate and hard to reproduce. Some alterations to the trial as well as holding jigs have been tried with varying degrees of success. Patient size and position also contribute to inaccuracy. Finally there is the difficulty of making measurements based on landmarks that are fairly distant such as the transcondylar axis at the distal humerus and forearm external rotation as references for prosthetic rotation. Adding to the difficulty is the fact that once the final components are placed, either by cementing or in a press-fit fashion, there is no allowance for adjustment. The prosthesis position cannot be changed without significant structural risk to the shoulder bone stock. This causes significant delays in the procedure as the surgeon checks and re-checks the position of the trial, knowing that no changes can be made once the final prosthesis is secured in place.

The shoulder prosthesis system of the present invention, however, has a distinctive mechanism that simplifies the procedure and allows for adjustment of these critical factors with the final prosthesis. The procedure and method for placement of the shoulder prosthesis follows. The process of describing the procedure will also outline the key design features of the system.

Procedure

Figure 30:
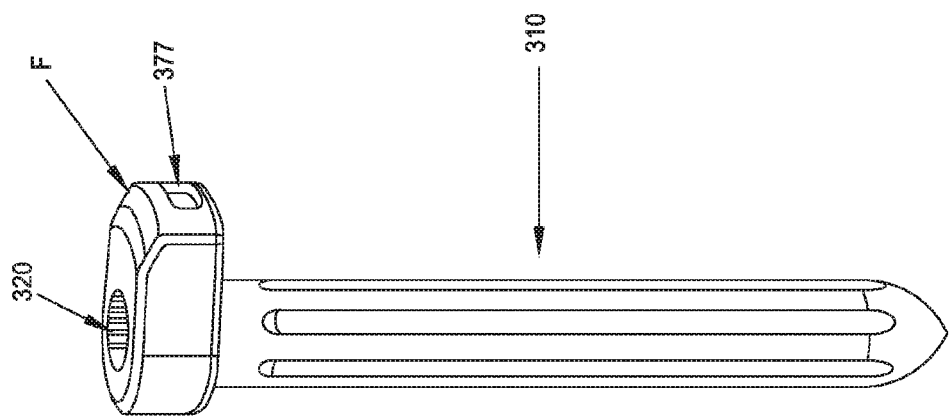

The first step in the procedure is to prepare the humeral shaft. This is done by reaming the intramedullary canal to create space for and determine the size of the initial component. This initial component is a tubular sleeve with a flange-like collar at its top end, e.g., the aforementioned sleeve 310. See FIG. 30. Note that, the tubular sleeve 310 shown in FIG. 30 is substantially the same as the sleeve 310 disclosed above, except that the flange-like collar F shown in FIG. 30 is not circular. More particularly, the flange-like collar F is preferably extended radially outwardly in the portion containing threaded keyway 377, whereby to make the key lock 382 disposed in threaded keyway 377 more easily accessible to the surgeon.

Figure 31:
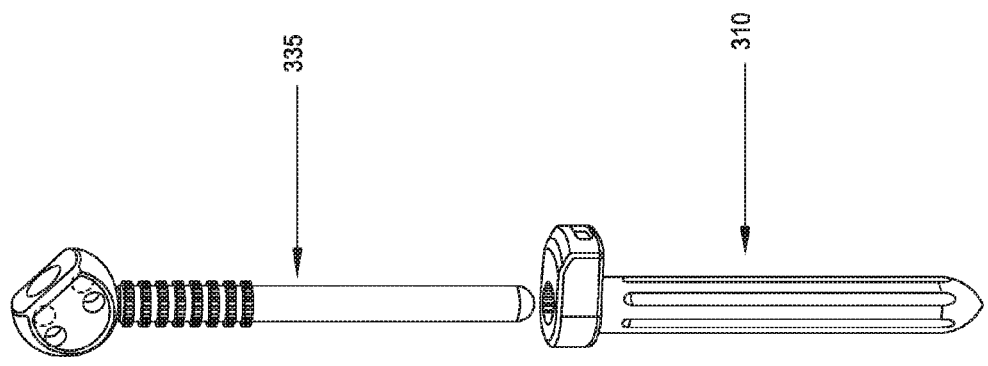

The sleeve will be cemented into place in the same fashion as for all prosthesis of the shoulder. The sleeve is cemented fully seated down to its collar and need only be cemented in a position that allows access to the key lock portion of the collar (described below). The sleeve's collar is preferably protected by a separate cover (not shown) during the cementing procedure in order to prevent cement from getting into the mechanisms on the collar which are used to secure the center adapter to the collar. Once the cement is hardened and all extraneous cement is removed, the protective cover is removed. It is into this sleeve that the prosthesis stem (e.g., the aforementioned center adapter 335) is placed. See FIG. 31.

The sleeve diameter selected determines the corresponding prosthesis stem (e.g., center adapter) that will fit into the sleeve. Therefore, once the reaming is completed and determines the sleeve diameter, that in turn determines the prosthesis stem (e.g., center adapter) that fits the sleeve. No further trialing is necessary inasmuch as the sleeve and stem (e.g., center adapter) are provided as a matched set.

Figure 32:
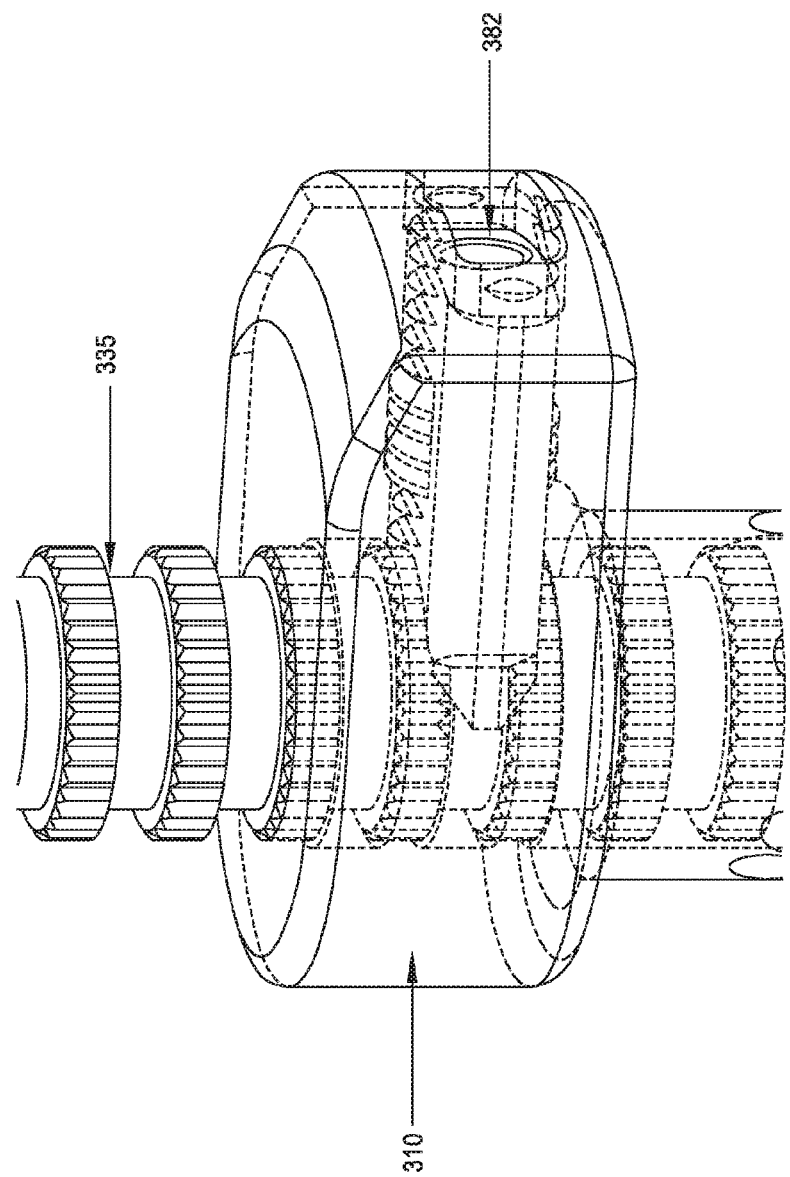

The upper portion of the sleeve and the shaft of the prosthesis stem (e.g., center adapter) have a mechanism that allows the coupling of the two components but also allows adjustment for both height and rotation. See, for example, FIG. 32, which shows the aforementioned sleeve 310 and the aforementioned center adapter 335. As discussed above, sleeve 310 comprises a plurality of horizontally-extending internal ribs 375 which are separated from one another by bands of recessed wall 376. Each of the horizontally-extending external ribs 375 carries a plurality of longitudinally-extending internal ribs 370 thereon. A threaded keyway 377 is formed in the side wall of sleeve 310. Threaded keyway 377 communicates with central lumen 320 of sleeve 310. As also discussed above, center adapter 335 comprises a plurality of horizontally-extending ribs 378 which are separated from one another by bands of recessed wall 379. Thus, the bands of recessed wall 379 essentially comprise horizontally-extending slots in center adapter 335. Each of the horizontally-extending ribs 378 carries a plurality of longitudinally-extending slots 381 thereon. And as also discussed above, the key lock 382 is radially movable along threaded keyway 377 via a screw 383 so as to secure center adapter 335 in a desired position relative to sleeve 310.

All known current prostheses do not allow any significant adjustment of the prosthesis after the cement has hardened. However, since with the present invention a cylindrical sleeve is installed first, it provides a foundation from which the stem (e.g., center adapter) can be adjusted. It is the aforementioned coupling mechanism between the sleeve and the stem (e.g., center adapter) that allows this adjustment option. This is a tremendous advantage to the surgeon and patient as the position of the articular surface can be optimized rather than having only one chance to estimate the proper position while cementing-in a final prosthesis that is firmly fixed after the cement hardens.

From the foregoing disclosure, it will be appreciated that, in one form of the invention, the coupling mechanism entails a series of splines on the shaft of the stem that match into corresponding splines on the upper portion of the sleeve. In one preferred form of the invention, there are three levels of splines within the sleeve to engage three levels of splines on the stem (e.g., center adapter). Engaging three levels of splines creates strength in resisting rotational force and also the top-to-bottom length of this engagement prevents toggle of the stem (e.g., center adapter) within the sleeve as well. These splines on each component are separated by a smooth recessed area. This smooth band is preferably laser-marked black to assist in demonstrating proper positioning of the stem (e.g., center adapter) for adjustment and locking options as described below. It will be appreciated that the distance between the spline bands sets the increment of height change, and the number of splines determines the increment of rotational adjustment. The coupling mechanism is preferably constructed so that it allows rotational adjustment in 10 degree increments and height adjustment in 4 mm increments. The sleeve has a locking key that is driven by a screw mechanism. As the screw is turned in a clockwise direction, it drives the locking key toward the center of the sleeve. When the stem (e.g., center adapter) is aligned with a dark laser-marked smooth area exposed immediately above the flange-like collar F, this is the locking position. In this position, the splines on the stem (e.g., center adapter) are engaged with the splines on the sleeve and a smooth area is aligned with the entry window of the locking key. As the locking key advances forward, it fits into the smooth area on the shaft of the stem (e.g., center adapter) below the first engaged spline at the top of the sleeve. With the locking key tightened into place, this holds the prosthesis stem (e.g., center adapter) within the sleeve, preventing any superior or inferior movement of the stem (e.g., center adapter). At the same time, in this position, the splines are engaged as well, locking the prosthesis in rotation.

If adjustment is desired, then the key lock is backed up to disengage the prosthesis stem (e.g., center adapter). The stem can then glide superiorly or inferiorly to adjust the height of the prosthesis. If rotational adjustment is desired, then the stem (e.g., center adapter) is held so one of the splines aligns with the superior rim of the sleeve. This puts the splines in alignment with the smooth bands and thus they do not engage. In this way rotation can be adjusted. When the desired rotation is obtained, then the stem (e.g., center adapter) is moved either superiorly or inferiorly so the splines engage at the desired height. The key lock is advanced, with the stem (e.g., center adapter) held in the locking position, and a laser-marked black smooth band aligned at the top edge of the sleeve.

Figure 33:
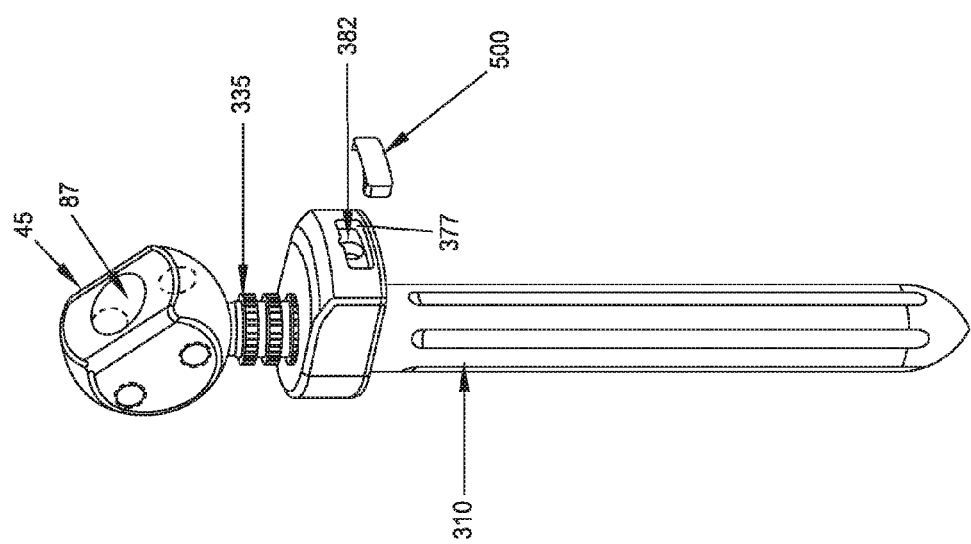

When the final desired height and rotation are obtained, and the key lock is tightened into place, a locking cover 500 (FIG. 33) is preferably applied to the sleeve so as to close off keyway 377. This locking cover fits into grooves which are formed within the window for the key lock on the sleeve. See FIG. 33. The locking cover covers the key lock, abutting against it and preventing back-out of the key lock. If the key lock cannot move backward, then the coupling mechanism remains secure. However, even at this stage, the locking cover 500 can be easily removed from the sleeve and allow access to the key lock if needed. The locking cover 500 preferably has scallops at its superior and inferior margins in order to accommodate a flat removal tool. This removal tool can easily lever out the locking cover if further adjustment of the prosthesis is deemed necessary. Therefore the surgeon can make adjustments to the prosthesis position at any time in the procedure and is never at a point where this option is eliminated.

Re-attachment of soft tissue and bone are frequently needed in a joint restoration procedure, particularly in the instance of a fracture. The greater and lesser tuberosity fragments have the tendons of the rotator cuff muscles attached to them. They are usually re-attached by suturing them to the prosthesis and the shaft of the bone. However, there is a high failure rate of the tuberosities uniting. Because a prosthesis is made of metal, and while it is often coated with a substance to enhance healing, it is difficult for fractured bone to heal to such a surface. This is made worse by the fact that there is frequently diminished surface area contact between the bone and such a surface. Some prostheses allow for some bone graft to be placed through a window in the prosthesis to facilitate bone-to-bone healing. This has improved tuberosity union rates, confirming that the concept is sound. However, the shape of such a bone plug in a small window on the prosthesis also does not allow enough surface area to allow good opportunity for healing.

To address this issue, the shoulder prosthesis of the present invention preferably has an optional bone cage that can be applied to the back of the prosthesis, e.g., the cage 90 previously discussed. See FIG. 34. This cage can be packed with bone graft or similar bone substitute and/or osteoconductive material. The windows of the bone cage are shaped and sized to maximize contact of the graft and the native bone being applied. The bone graft could be packed separately in a holding bowl that could stabilize the cage. Once the bone graft is sufficiently packed, it can be compressed with a tamp that is shaped like the back side of the prosthesis in order to ensure proper fit once the cage was applied to the prosthesis. With the graft packing completed, the cage can then be applied to the prosthesis and secured with a screw, e.g., screw 91. Significantly, because the bone cage is preferably shaped so as to follow the contours of the back of the prosthesis stem, the forces on the screw are dispersed. In addition, there is preferably a slight offset between the threaded hole in the prosthesis (e.g., the aforementioned hole 93) and the hole in the back of the bone cage (e.g., the aforementioned hole 92). As the screw fully seats, it places some tension on the bone cage. This tension, which places a lateral force on the shaft of the screw, will prevent the screw from backing out. The bone cage preferably also has multiple attachment points for suturing of the tuberosities to the prosthesis in order to ensure secure hold and apposition to the graft.

Figure 34:
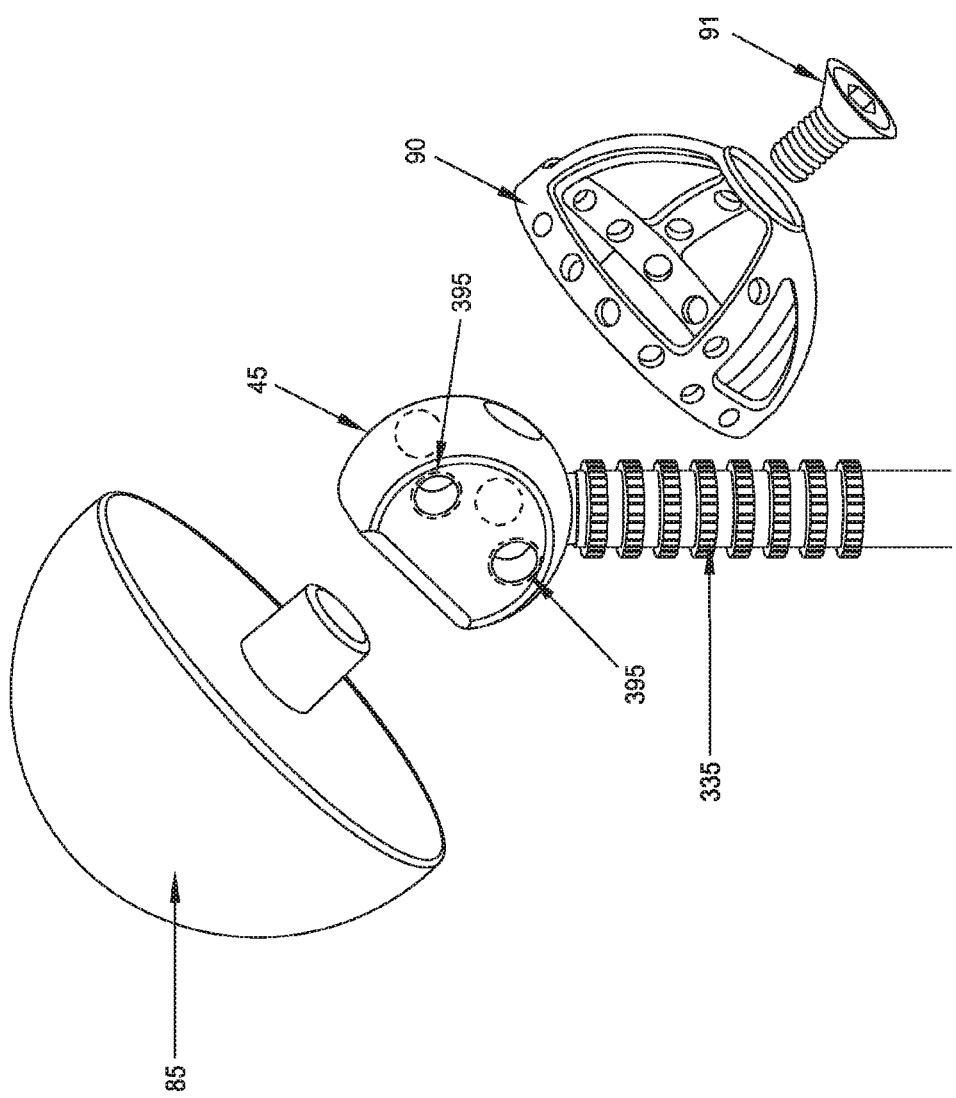
Figure 35:
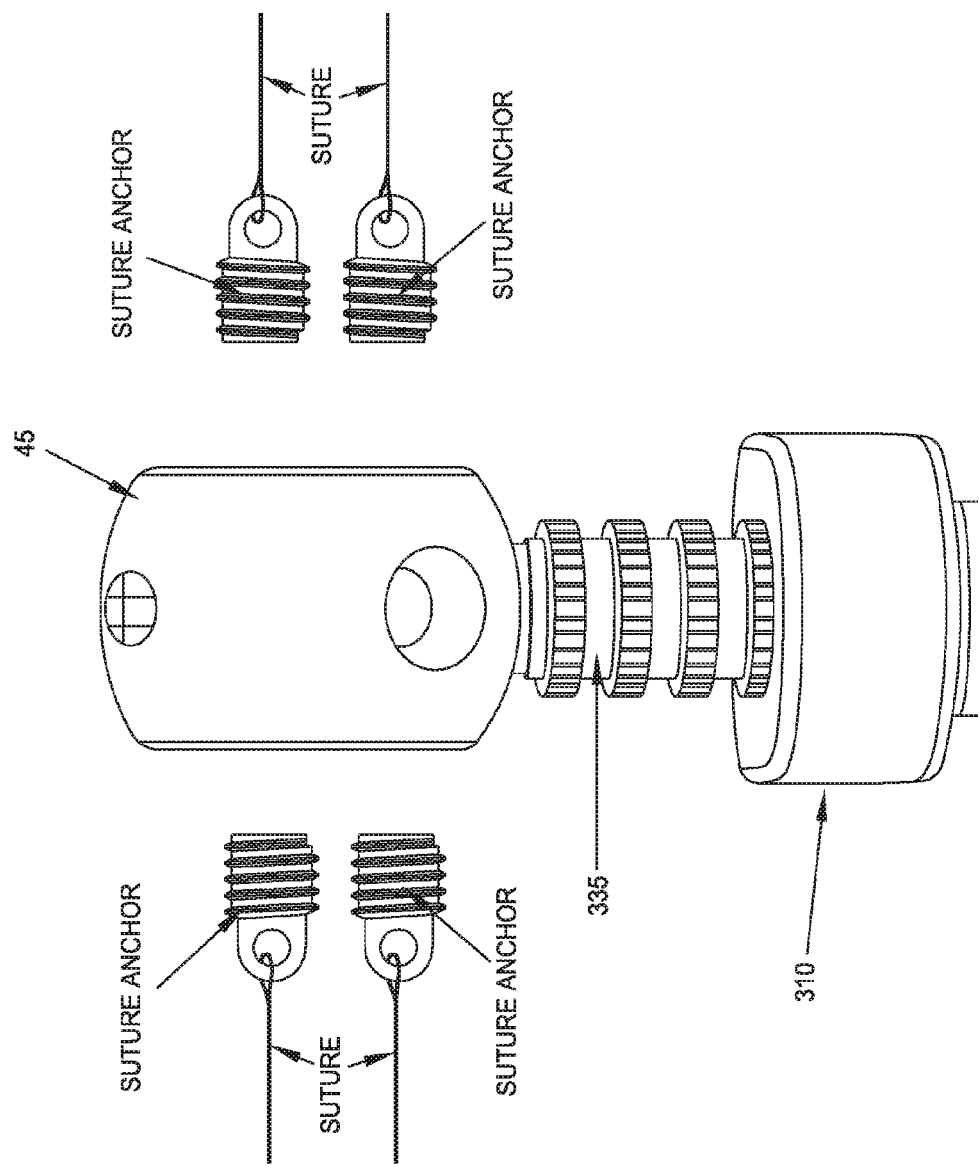

An additional feature that is present to enhance attachment of bone and soft tissue to the prosthesis are optional suture anchors (FIG. 35) that can be placed in threaded holes on the prosthesis stem's head portion, e.g., the threaded holes 395 shown in FIG. 34. See, for example, FIG. 36., which shows bone anchors (with attached suture) disposed in head 45. These suture anchors can be placed anteriorly as well as posteriorly. Because the stem (e.g., center adapter) of the prosthesis can be rotated and adjusted at any time, this allows access to the posterior aspect of the prosthesis for anchoring of the tuberosities in a fracture setting.

Normally, with the prosthesis fixed in place, it is very difficult to access the posterior aspect and all of the anchoring is applied to the anterior accessible aspect. These additional features increase the choices available to the surgeon to achieve bony and soft tissue union in this very difficult reconstructive environment. Because these features are optional, the surgeon can use them at his/her discretion to address the situation at hand.

Applicable Joints

It will be appreciated that the prosthesis of the present invention may be used in a variety of joints within the body, e.g., the elbow, the wrist, the distal radius, proximal radius, hip, etc.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. A joint prosthesis for mounting in a first bone and presenting a prosthetic joint surface for engaging an opposing joint surface of a second bone, the joint prosthesis comprising:
   a sleeve which is adapted for partial disposition in an opening formed in the first bone;
   a center adapter which is adapted for disposition within the sleeve, the center adapter comprising an elongated shaft terminating in a head having a first side adapted to face the joint surface of a patient's second bone, and a second side adapted to face away from the joint surface of the patient's second bone;

a prosthetic joint surface mounted to the first side of the head of the center adapter, wherein the prosthetic joint surface comprises a hemispherical structure, and further wherein the prosthetic joint surface is mounted to the first side of the head of the center adapter so that the hemispherical structure contacts the joint surface of the second bone; and a cage mounted to the second side of the head of the center adapter, wherein the cage comprises a hemispherical structure;

wherein the disposition of the center adapter is adjustable, both longitudinally and rotationally, relative to the sleeve, so that the disposition of the prosthetic joint surface is adjustable, both longitudinally and rotationally, relative to the opposing joint surface of the second bone.

2. A joint prosthesis according to claim 1 wherein the opening comprises the intramedullary canal of the first bone.

3. A joint prosthesis according to claim 1 wherein the hemispherical structure comprises the ball of a ball-and-socket joint.

4. A joint prosthesis according to claim 1 wherein the sleeve comprises a first body and a second body, wherein the first body comprises the central lumen and the second body comprises the horizontally-extending rib and the longitudinally-extending rib, and further wherein the second body is selectively securable to the first body.

5. A joint prosthesis according to claim 4 wherein the first body of the sleeve comprises a crown having a peripheral detent formed therein, wherein the second body of the sleeve comprises a collar having a nib formed thereon, and further wherein the second body of the sleeve is secured to the first body of the sleeve when the nib is disposed in the peripheral detent.

6. A joint prosthesis according to claim 5 wherein the second body of the sleeve comprises two halves selectively secured together.

7. A joint prosthesis according to claim 4 wherein the longitudinally-extending rib is formed on the horizontally-extending rib.

8. A joint prosthesis according to claim 7 wherein the first body of the sleeve comprises the central lumen and the second body of the sleeve comprises the horizontally-extending rib and a longitudinally-extending rib, and further wherein the second body of the sleeve is selectively securable to the first body.

9. A joint prosthesis according to claim 7 wherein the second body of the sleeve comprises two halves pivotally secured to the first body.

10. A joint prosthesis according to claim 7 wherein the two halves latch to one another.

11. A joint prosthesis according to claim 7 wherein the plurality of horizontally-extending slots of the center adapter and the plurality of longitudinally-extending slots of the center adapter are superimposed upon one another.

12. A joint prosthesis according to claim 1 wherein the joint prosthesis further comprises an opening for receiving a suture anchor therein.

13. A joint prosthesis according to claim 1 further comprising a screw for mounting the cage to the second side of the head of the center adapter.

14. A joint prosthesis according to claim 1 wherein the cage comprises at least one window.

15. A joint prosthesis according to claim 1 wherein the cage comprises at least one attachment point for receiving a suture.

16. A method for restoring a joint, the method comprising:
providing a joint prosthesis for mounting in a first bone and presenting a prosthetic joint surface for engaging an opposing joint surface of a second bone, the joint prosthesis comprising:
a sleeve which is adapted for disposition in an opening formed in the first bone;
a center adapter which is adapted for partial disposition within the sleeve, the center adapter comprising an elongated shaft terminating in a head having a first side adapted to face the joint surface of a patient's second bone, and a second side adapted to face away from the joint surface of the patient's second bone; and
a prosthetic joint surface mounted to the first side of the head of the center adapter, wherein the prosthetic joint surface comprises a hemispherical structure, and further wherein the prosthetic joint surface is mounted to the first side of the head of the center adapter so that the hemispherical structure contacts the joint surface of the second bone; and
a cage mounted to the second side of the head of the center adapter, wherein the cage comprises a hemispherical structure;
wherein the disposition of the center adapter is adjustable, both longitudinally and rotationally, relative to the sleeve, so that the disposition of the prosthetic joint surface is adjustable, both longitudinally and rotationally, relative to the opposing joint surface of the second bone;
forming an opening in the first bone;
deploying a sleeve in the opening formed in the first bone;
positioning a center adapter partially within the sleeve;
adjusting the longitudinal and rotational position of the center adapter with respect to the sleeve; and
securing the center adapter to the sleeve.

* * * * *